US010836782B2

(12) United States Patent
Kalyanaraman et al.

(10) Patent No.: US 10,836,782 B2
(45) Date of Patent: Nov. 17, 2020

(54) MITO-HONOKIOL COMPOUNDS AND METHODS OF SYNTHESIS AND USE THEREOF

(71) Applicants: THE MEDICAL COLLEGE OF WISCONSIN, INC., Milwaukee, WI (US); AIX-MARSEILLE UNIVERSITE, Marseilles (FR)

(72) Inventors: Balaraman Kalyanaraman, Milwaukee, WI (US); Jacek Michal Zielonka, Wauwatosa, WI (US); Micael J. Hardy, Nimes (FR); Oliver Ouari, Marseilles (FR); Ming You, Elm Grove, WI (US)

(73) Assignees: The Medical College of Wisconsin, Inc., Milwaukee, WI (US); Aix-Marseille Universite, Marseilles (FR)

( * ) Notice: Subject to any disclaimer, the term of this patent is extended or adjusted under 35 U.S.C. 154(b) by 0 days.

(21) Appl. No.: 15/735,405

(22) PCT Filed: Jun. 10, 2016

(86) PCT No.: PCT/US2016/036827
§ 371 (c)(1),
(2) Date: Dec. 11, 2017

(87) PCT Pub. No.: WO2016/201188
PCT Pub. Date: Dec. 15, 2016

(65) Prior Publication Data
US 2018/0134737 A1 May 17, 2018

Related U.S. Application Data

(60) Provisional application No. 62/174,185, filed on Jun. 11, 2015.

(51) Int. Cl.
| | | |
|---|---|---|
| C07F 9/54 | (2006.01) | |
| A61K 31/66 | (2006.01) | |
| A61P 35/00 | (2006.01) | |
| A61K 45/06 | (2006.01) | |
| A61K 31/19 | (2006.01) | |
| A61K 31/7004 | (2006.01) | |

(52) U.S. Cl.
CPC ............ *C07F 9/5442* (2013.01); *A61K 31/19* (2013.01); *A61K 31/66* (2013.01); *A61K 31/7004* (2013.01); *A61K 45/06* (2013.01); *A61P 35/00* (2018.01); *C07F 9/5449* (2013.01); *A61K 2300/00* (2013.01)

(58) Field of Classification Search
CPC ....... C07F 9/5442; C07F 9/5449; A61K 31/66
See application file for complete search history.

(56) References Cited

U.S. PATENT DOCUMENTS

| 8,586,627 B2 | 11/2013 | Arbiser |
| 8,822,531 B2 | 9/2014 | Arbiser |
| 2004/0105906 A1 | 6/2004 | Arbiser et al. |
| 2008/0300298 A1 | 12/2008 | Arbiser et al. |

FOREIGN PATENT DOCUMENTS

| WO | 99/00346 | 1/1999 |
| WO | 00/40532 | 7/2000 |
| WO | 2015/066432 | 5/2015 |

OTHER PUBLICATIONS

MedicineNet.com (2004) Web: <http://www.medterms.com> (Year: 2004).*
Alas et al. (2003). Inhibition of constitutive STAT3 activity sensitizes resistant non-Hodgkin's lymphoma and multiple myeloma to chemotherapeutic drug-mediated apoptosis. Clin Cancer Res 9, 316-326.
Anders et al. (2015). HTSeq—a Python framework to work with high-throughput sequencing data. Bioinformatics 31, 166-169.
Bewry et al. (2008). Stat3 contributes to resistance toward BCR-ABL inhibitors in a bone marrow microenvironment model of drug resistance. Mol Cancer Ther 7, 3169-3175.
Bradford et al. (2013). RNA-Seq Differentiates Tumour and Host mRNA Expression Changes Induced by Treatment of Human Tumour Xenografts with the VEGFR Tyrosine Kinase Inhibitor Cediranib. PLoS One 8, e66003.
Chen et al. (2004). Honokiol: a potent chemotherapy candidate for human colorectal carcinoma. World J Gastroenterol 10, 3459-3463.
Chen et al. (2010). Honokiol induces cell apoptosis in human chondrosarcoma cells through mitochondrial dysfunction and endoplasmic reticulum stress. Cancer Lett 291, 20-30.
Cheng et al. (2012). Mitochondria-targeted drugs synergize with 2-deoxyglucose to trigger breast cancer cell death. Cancer Res 72, 2634-2644.
Cheng et al. (2014). Profiling and targeting of cellular bioenergetics: inhibition of pancreatic cancer cell proliferation. Br J Cancer, 1-9.
Cheng et al. (2013). Mitochondria-targeted vitamin E analogs inhibit breast cancer cell energy metabolism and promote cell death. BMC Cancer 13, 285-285.
Crane et al. (2009). Honokiol-mediated inhibition of PI3K/mTOR pathway: a potential strategy to overcome immunoresistance in glioma, breast, and prostate carcinoma without impacting T cell function. J Immunother 32, 585-592.
De Simone et al. (2015). Th17-type cytokines, IL-6 and TNF-alpha synergistically activate STAT3 and NF-kB to promote colorectal cancer cell growth. Oncogene 34, 3493-3503.
Deng et al. (2008). Involvement of p38 mitogen-activated protein kinase pathway in honokiol-induced apoptosis in a human hepatoma cell line (hepG2). Liver Int 28, 1458-1464.
Gane et al. (2010). The mitochondria-targeted anti-oxidant mitoquinone decreases liver damage in a phase II study of hepatitis C patients. Liver Int 30, 1019-1026.

(Continued)

*Primary Examiner* — Emily A Bernhardt
*Assistant Examiner* — Laura M Daniel
(74) *Attorney, Agent, or Firm* — Quarles & Brady LLP

(57) ABSTRACT

The present invention provides mito-honokiol compounds, pharmaceutical compositions thereof, and methods of using the mito-honokiol compounds in the treatment of cancer.

27 Claims, 21 Drawing Sheets

(56) References Cited

OTHER PUBLICATIONS

Garcia et al. (2008). Honokiol suppresses survival signals mediated by Ras-dependent phospholipase D activity in human cancer cells. Clin Cancer Res 14, 4267-4274.
Goldberg et al. (2015). Lung Cancer Brain Metastases. Cancer J 21, 398-403.
Hahm et al. (2007). Honokiol causes G0-G1 phase cell cycle arrest in human prostate cancer cells in association with suppression of retinoblastoma protein level/phosphorylation and inhibition of E2F1 transcriptional activity. Mol Cancer Ther 6, 2686-2695.
Jemal et al. (2010). Cancer statistics, 2010. CA: a cancer journal for clinicians 60, 277-300.
Koizumi et al. (2005). Establishment of a human non-small cell lung cancer cell line resistant to gefitinib. Int J Cancer 116, 36-44.
Langmead et al. (2009). Ultrafast and memory-efficient alignment of short DNA sequences to the human genome. Genome Biol 10, R25.
Lee et al. (2014). Drug resistance via feedback activation of Stat3 in oncogene-addicted cancer cells. Cancer Cell 26, 207-221.
Lee et al. (2016). Inhibition of IGF1R signaling abrogates resistance to afatinib (BIBW2992) in EGFR T790M mutant lung cancer cells. Mol Carcinog 55, 991-1001.
Li et al. (2016). Redox homeostasis protects mitochondria through accelerating ROS conversion to enhance hypoxia resistance in cancer cells. Sci Rep 6, 22831.
Lin et al. (2012). Honokiol traverses the blood-brain barrier and induces apoptosis of neuroblastoma cells via an intrinsic bax-mitochondrion-cytochrome c-caspase protease pathway. Neuro Oncol 14, 302-314.
Lin et al. (2011). STAT3 is necessary for proliferation and survival in colon cancer-initiating cells. Cancer Res 71, 7226-7237.
Martin et al. (2013). Inducing apoptosis of cancer cells using small-molecule plant compounds that bind to GRP78. Br J Cancer 109, 433-443.
McManus et al. (2011). The mitochondria-targeted antioxidant MitoQ prevents loss of spatial memory retention and early neuropathology in a transgenic mouse model of Alzheimer's disease. J Neurosci 31, 15703-15715.
Nair et al. (2012). Role of STAT3 in Transformation and Drug Resistance in CML. Front Oncol 2, 30.
Nguyen et al. (2009). WNT/TCF signaling through LEF1 and HOXB9 mediates lung adenocarcinoma metastasis. Cell 138, 51-62.
Pan et al. (2014). Honokiol inhibits lung tumorigenesis through inhibition of mitochondrial function. Cancer Prev Res (Phila) 7, 1149-1159.
Park et al. (2009). Down-regulation of c-Src/EGFR-mediated signaling activation is involved in the honokiol-induced cell cycle arrest and apoptosis in MDA-MB-231 human breast cancer cells. Cancer Lett 277, 133-140.
Phelps et al. (1996). NCI-Navy Medical Oncology Branch cell line data base. J Cell Biochem Suppl 24, 32-91.
Pillai et al. (2015). Honokiol blocks and reverses cardiac hypertrophy in mice by activating mitochondrial Sirt3. Nat Commun 6, 6656.
Robinson et al. (2010). edgeR: a Bioconductor package for differential expression analysis of digital gene expression data. Bioinformatics 26, 139-140.
Rossello et al. (2013). Next-generation sequence analysis of cancer xenograft models. PLoS One 8, e74432.
Trapnell et al. (2009). TopHat: discovering splice junctions with RNA-Seq. Bioinformatics 25, 1105-1111.
Tsai et al. (1994). Pharmacokinetics of honokiol after intravenous administration in rats assessed using high-performance liquid chromatography. J Chromatogr B Biomed Appl 655, 41-45.
Vazquez-Martin et al. (2013). IGF-1R/epithelial-to-mesenchymal transition (EMT) crosstalk suppresses the erlotinib-sensitizing effect of EGFR exon 19 deletion mutations. Sci Rep 3, 2560.
Wang et al. (2011). Honokiol crosses BBB and BCSFB, and inhibits brain tumor growth in rat 9L intracerebral gliosarcoma model and human U251 xenograft glioma model. PLoS One 6, e18490.
Yang et al. (2015). STAT3 Inhibition Enhances the Therapeutic Efficacy of Immunogenic Chemotherapy by Stimulating Type 1 Interferon Production by Cancer Cells. Cancer Res 75, 3812-3822.
Yau et al. (2005). Inhibition of integrin-linked kinase by a selective small molecule inhibitor, QLT0254, inhibits the PI3K/PKB/mTOR, Stat3, and FKHR pathways and tumor growth, and enhances gemcitabine-induced apoptosis in human orthotopic primary pancreatic cancer xenografts. Cancer Res 65, 1497-1504.
Yu et al. (2015). Reversal of doxorubicin resistance in breast cancer by mitochondria-targeted pH-responsive micelles. Acta Biomater 14, 115-124.
Zhang et al. (2013). Mitochondrial localized Stat3 promotes breast cancer growth via phosphorylation of serine 727. J Biol Chem 288, 31280-31288.
Zhou et al. (2007). Activation of the PTEN/mTOR/STAT3 pathway in breast cancer stem-like cells is required for viability and maintenance. Proc Natl Acad Sci U S A 104, 16158-16163.
Lee et al. (2011) Therapeutic applications of compounds in the Magnolia family. Pharmacol. Ther., 130, 157-176.
Shigemura et al. (2007) Honokiol, a natural plant product, inhibits the bone metastatic growth of human prostate cancer cells. Cancer, 109, 1279-1289.
Woodbury et al. (2013) Neuro-modulating effects of honokiol: a review. Front. Neurol., 4, 130.
Fried et al. (2009) Honokiol, a multifunctional antiangiogenic and antitumor agent. Antioxid. Redox Signal., 11, 1139-1148.
Arora et al. (2012) Honokiol: a novel natural agent for cancer prevention and therapy. Curr. Mol. Med., 12, 1244-1252.
Ramsay et al. (2011) Pharm. Res., 28, 2731-2744.
Murphy et al. (2007) Targeting antioxidants to mitochondria by conjugation to lipophilic cations. Annu. Rev. Pharmacol. Toxicol., 47, 629-656.
Tse et al. (2005). Honokiol inhibits TNF-alpha-stimulated NF-kappaB activation and NF-kappaB-regulated gene expression through suppression of IKK activation. Biochem Pharmacol 70, 1443-1457.
Wu et al. (2014). EGFR-STAT3 signaling promotes formation of malignant peripheral nerve sheath tumors. Oncogene 33, 173-180.
Lin et al. (2012) In vitro growth inhibition of human cancer cells by novel honokiol analogs. Bioorg. Med. Chem., 20, 3202-3211.
Ma et al. (2011) Structural modification of honokiol, a biphenyl occurring in Magnolia officinalis: the evaluation of honokiol analogues as inhibitors of angiogenesis and for their cytotoxicity and structure-activity relationship. J. Med. Chem., 54, 6469-6481.
Perche et al. (2013) published on-line 2013:705265.
Hu et al. (2008) Liposomal honokiol, a potent anti-angiogenesis agent, in combination with radiotherapy produces a synergistic antitumor efficacy without increasing toxicity. Exp Mol Med. 40:617-28. Hu J. et al.
Bai et al. (2003) Honokiol, a small molecular weight natural product, inhibits angiogenesis in vitro and tumor growth in vivo. J Biol Chem. 278:35501-7.
International Search Report and Written Opinion for International Patent Application No. PCT/US2016/036827 dated Nov. 3, 2016.

\* cited by examiner

Inhibition of Mitochondrial Complex I Activity

Figure 7
A. H2030BrM3
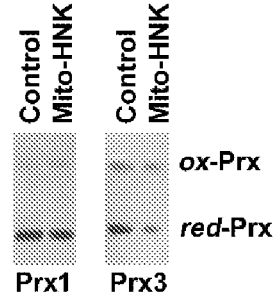
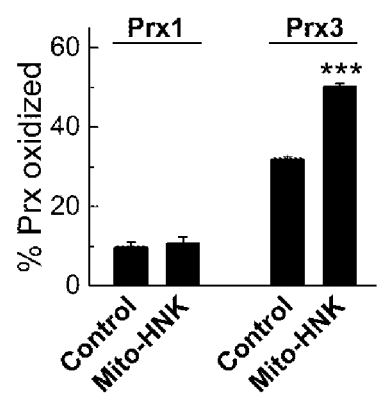
B. DMS273
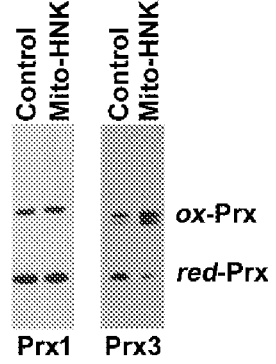
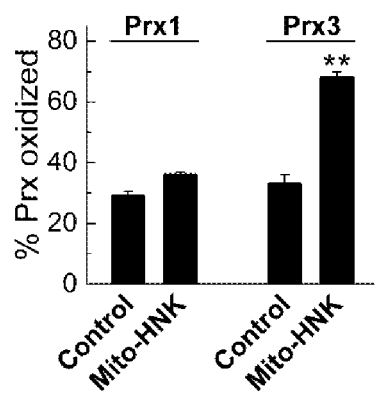

Mito-Honokiol Exhibits Sub-Micromolar Potency on Lung Cancer Cell Proliferation, Migration and Invasion

Role of STAT3/Complex I in Mediating Mito-Honokiol's Inhibitory Effects

Figure 11. Mito-HNK exhibits potent anti-cancer efficacy in an orthotopic lung can model U87 Cells MiaPaCa-2 cells MiaPaCa-2 cells Capan-2 Cells Total ATP Total ATP

MITO-HONOKIOL COMPOUNDS AND METHODS OF SYNTHESIS AND USE THEREOF

CROSS-REFERENCE TO RELATED APPLICATIONS

This application represents the national stage entry of PCT International Application No. PCT/US2016/036827 filed on Jun. 10, 2016 and claims priority to U.S. Provisional Patent Application No. 62/174,185 filed on Jun. 11, 2015, the contents of which are incorporated by reference in its entirety.

STATEMENT REGARDING FEDERALLY SPONSORED RESEARCH OR DEVELOPMENT

Not Applicable.

FIELD OF THE INVENTION

This invention relates generally to mitochondria-targeting cationic drugs, specifically to mito-honokiol compounds, and methods of using the mito-honokiol compounds to treat cancer.

BACKGROUND

Honokiol is a natural biphenolic compound present in Magnolia bark extracts that has been reported to exert antitumor effects in several in vitro and in vivo models of cancer (e.g. melanoma, myeloma, lung, prostate). While the mechanism of this activity is currently under investigation, emerging evidence points to mitochondrial effects of honokiol, leading to decreased cellular respiration and decreased cellular energy status (decreased ATP and increased AMP levels).

Previous attempts to improve and enhance the efficacy of honokiol have involved modified honokiol to inhibit angiogenesis. However, these previous efforts have resulted in significant negative side effects, and have not been successful.

Linking therapeutics to triphenylphosphonium (TPP) has been shown to increase the accumulation of a wide variety of compounds into mitochondria. TPP cations possess lipophilic character and therefore cross cellular membranes and accumulate into mitochondria due to the enhanced negative membrane potential of tumor mitochondria. The long alkyl chain linking honokiol to TPP moieties has two advantages: (a) it increases the lipophilic character of the compound, leading to an enhanced cellular uptake; and (b) it separates in space the bulky TPP moiety from the aromatic group of honokiol, minimizing the effect of substituents on the pharmacophore activity.

Therefore, a need exists for compounds that are effective in inhibiting tumor formation (i.e., reducing the severity or slowing the progression of symptoms of cancer) which have increased efficacy at lower doses while also mitigating resistance to chemo and radiotherapies.

SUMMARY OF THE INVENTION

In one embodiment, the invention comprises a mito-honokiol compound according to the following structure:

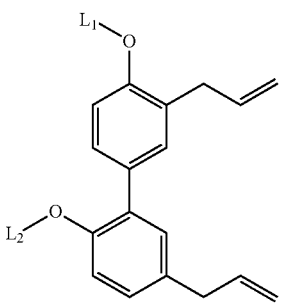

Where $L_1$ and/or $L_2$ is:

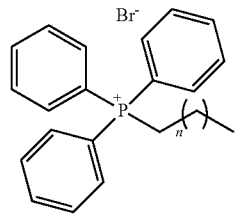

$n = 1\text{-}12$ where $L_1$ and $L_2$ cannot be H at the same time.

In alternate embodiments, the invention comprises a mito-honokiol compound according to the following structure:

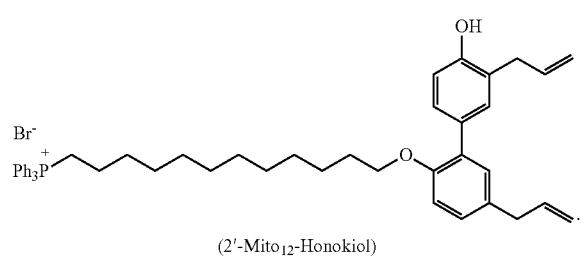

(2'-Mito$_{12}$-Honokiol)

In alternate embodiments, the invention comprises a mito-honokiol compound according to the following structure:

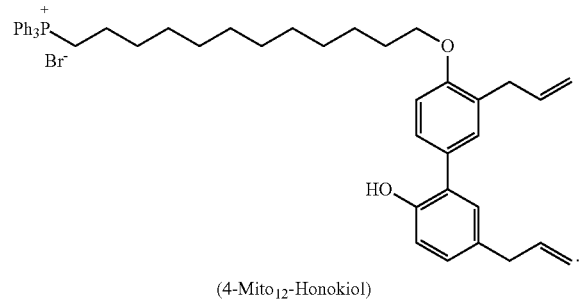

(4-Mito$_{12}$-Honokiol)

In alternate embodiments, the invention comprises a mito-honokiol compound according to the following structure:

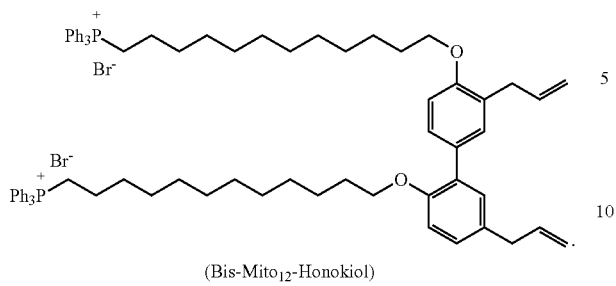

(Bis-Mito$_{12}$-Honokiol)

In alternate embodiments, the invention comprises a mito-honokiol compound according to the following structure:

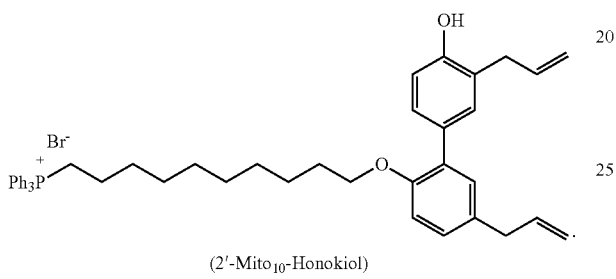

(2'-Mito$_{10}$-Honokiol)

In alternate embodiments, the invention comprises a mito-honokiol compound according to the following structure:

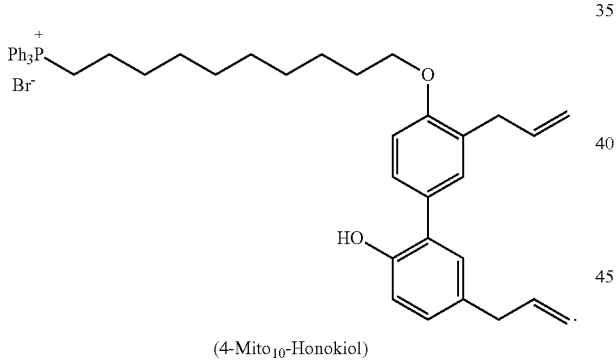

(4-Mito$_{10}$-Honokiol)

In alternate embodiments, the invention comprises a mito-honokiol compound according to the following structure:

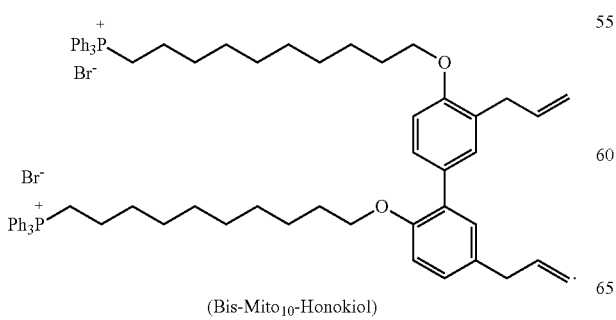

(Bis-Mito$_{10}$-Honokiol)

In alternate embodiments, the invention comprises a mito-honokiol compound according to the following structure:

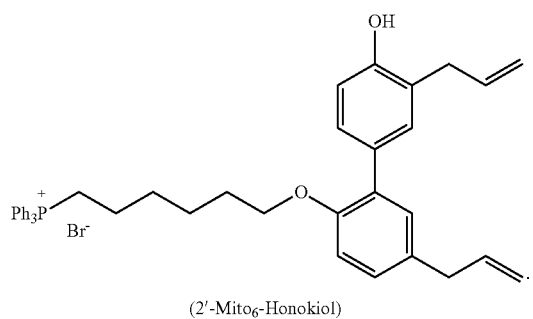

(2'-Mito$_6$-Honokiol)

In alternate embodiments, the invention comprises a mito-honokiol compound according to the following structure:

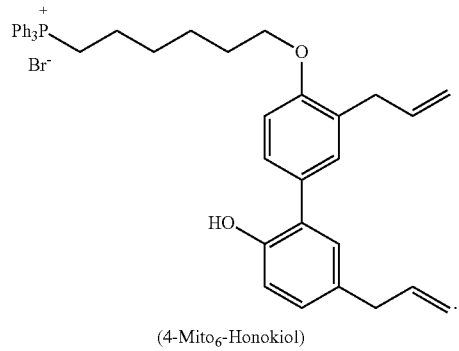

(4-Mito$_6$-Honokiol)

In alternate embodiments, the invention comprises a mito-honokiol compound according to the following structure:

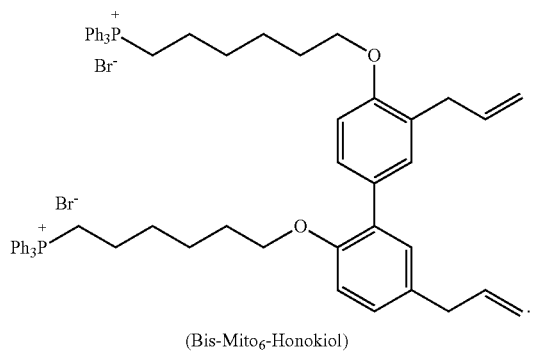

(Bis-Mito$_6$-Honokiol)

In alternate embodiments, the invention comprises a mito-honokiol compound according to the following structure:

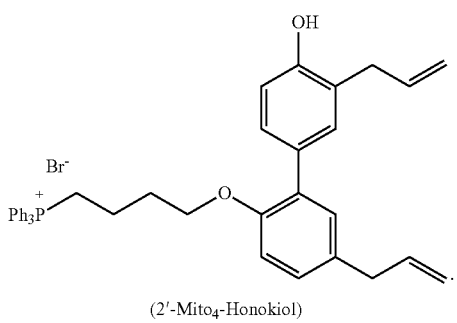

(2′-Mito₄-Honokiol)

In alternate embodiments, the invention comprises a mito-honokiol compound according to the following structure:

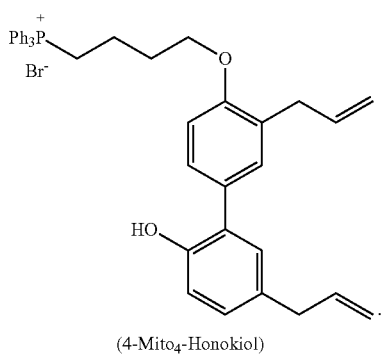

(4-Mito₄-Honokiol)

In alternate embodiments, the invention comprises a mito-honokiol compound according to the following structure:

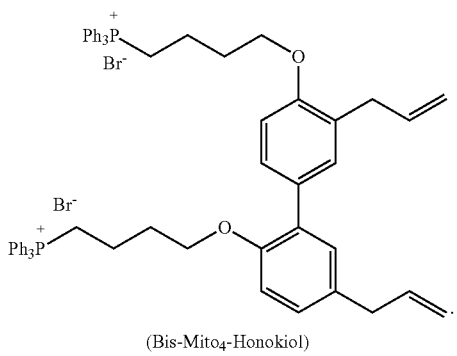

(Bis-Mito₄-Honokiol)

In alternate embodiments, the invention comprises a mito-honokiol compound according to the following structure:

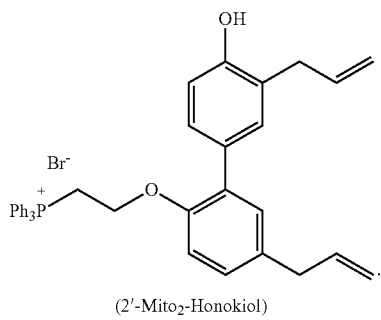

(2′-Mito₂-Honokiol)

In alternate embodiments, the invention comprises a mito-honokiol compound according to the following structure:

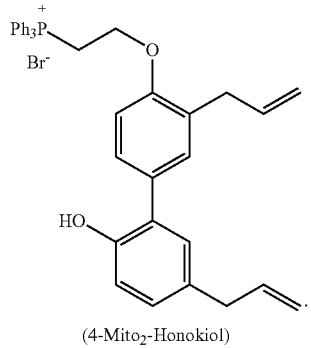

(4-Mito₂-Honokiol)

In alternate embodiments, the invention comprises a mito-honokiol compound according to the following structure:

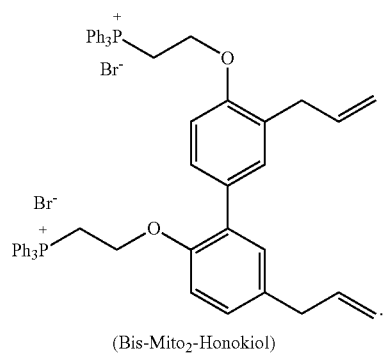

(Bis-Mito₂-Honokiol)

In alternate embodiments, the invention comprises a mito-honokiol compound according to the following structure:

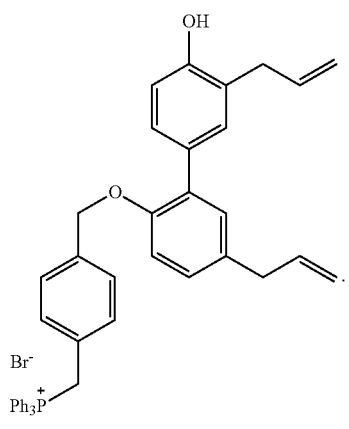

(2′-Mito*phen*-Honokiol)

In alternate embodiments, the invention comprises a mito-honokiol compound according to the following structure:

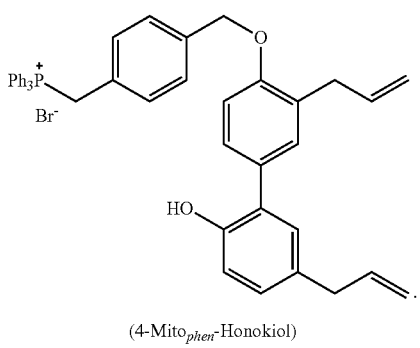

(4-Mito_phen-Honokiol)

In alternate embodiments, the invention comprises a mito-honokiol compound according to the following structure:

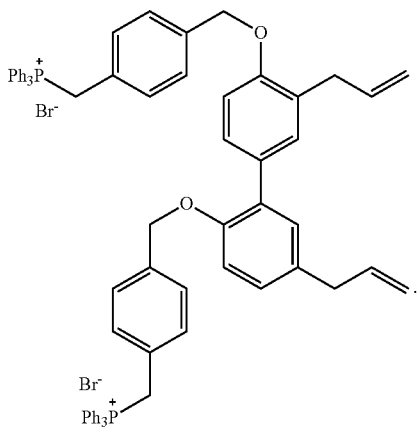

(Bis-Mito_phen-Honokiol)

In an alternate embodiments, the invention comprises mitochondria-targeted honokiol derivatives

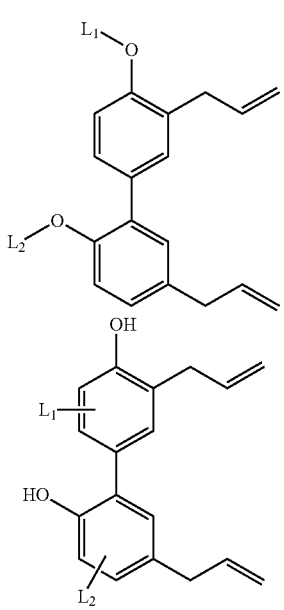

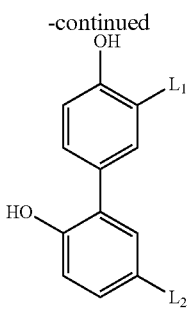

where $L_1$ and/or $L_2$ are comprised of organic linker attached to triphenylphosphonium moiety.

In some embodiments, $L_1$ and/or $L_2$ comprise an organic linker comprising about 1-15 carbons, preferably about 1-12 carbons, attached to the triphenylphosphonium moiety.

In an alternate embodiments, the invention comprises mitochondria-targeted magnolol derivatives

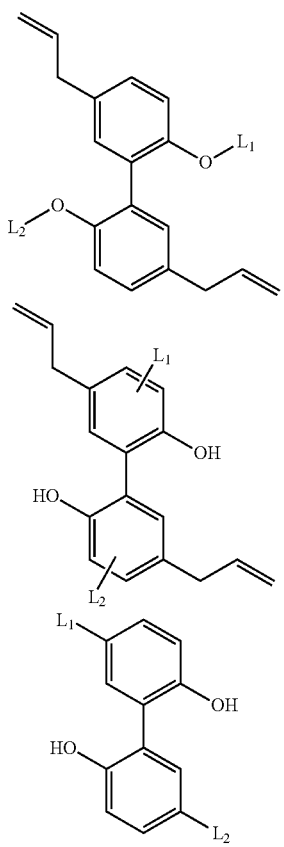

where $L_1$ and/or $L_2$ are comprised of organic linker attached to triphenylphosphonium moiety.

In some embodiments, $L_1$ and/or $L_2$ comprise an organic linker comprising about 1-15 carbons, preferably about 1-12 carbons, attached to the triphenylphosphonium moiety.

In alternate embodiments, the invention also comprises a method of inhibiting tumor formation in a subject comprising administering to the subject a therapeutically effective amount of a composition comprising at least one mito-honokiol compound as described above.

In an alternate embodiment, the invention comprises a method of protecting healthy cells in a subject having cancer. The method comprises administering to the subject a therapeutically effective amount of a composition comprising at least one mito-honokiol compound as described above. This neuroprotective effect of the mito-honokiol compounds of the presently claimed invention can be used in combination with other cancer treatments.

In alternate embodiments, the invention comprises a kit comprising at least one mito-honokiol compound as described above, a pharmaceutically acceptable carrier or diluent, and instructional material.

Other features of the present invention will become apparent after review of the specification, claims and drawings.

BRIEF DESCRIPTION OF THE DRAWINGS

FIG. 7A-B. Induction of mitochondrial peroxiredoxin-3 (Prx3) oxidation. 24-h treatment of H2030BrM3 (A) or DMS-273 (B) cells with Mito-HNK (0.2 μM and 0.4 μM, respectively) led to significant oxidation of mitochondrial Prx3, whereas the oxidation status of cytosolic Prx1 did not significantly change.

FIGS. 17A and 17B show the effects of the combination of mito-honokiols with 2-deoxyglucose on viability (total ATP) in Capan-2 cells (pancreatic adenocarcinoma cell line).

DETAILED DESCRIPTION OF THE INVENTION

In General.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

Figure 1:
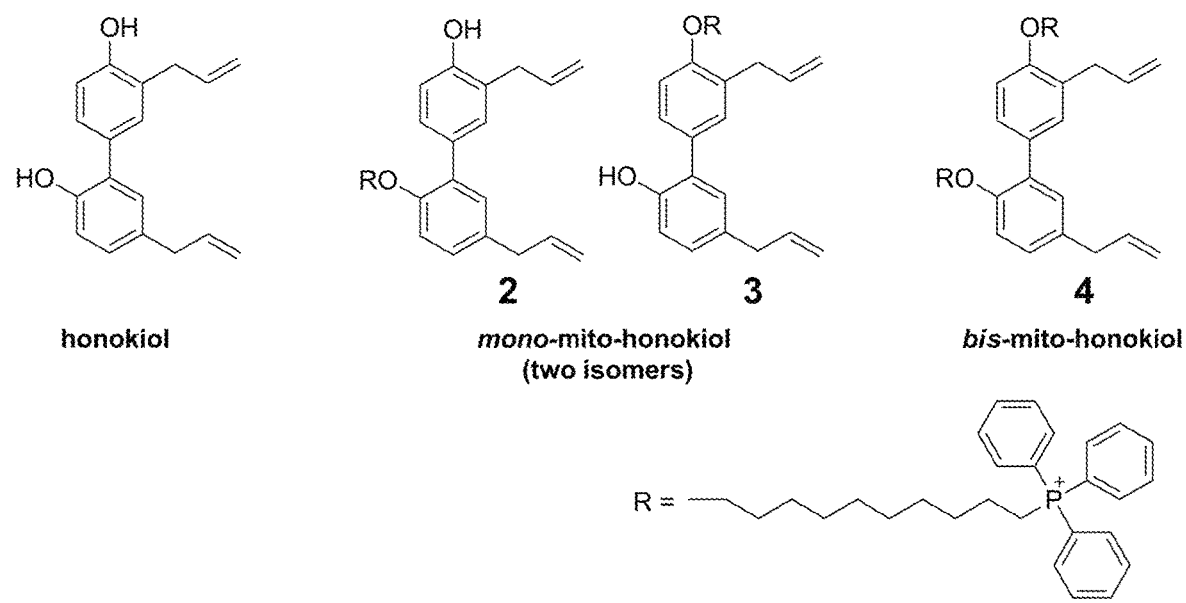
FIG. 1. Chemical structures of honokiol, and its mitochondria-targeted analogs. R=triphenylphosphonium (TPP) with an 10 carbon alkyl linker.
Figure 2:
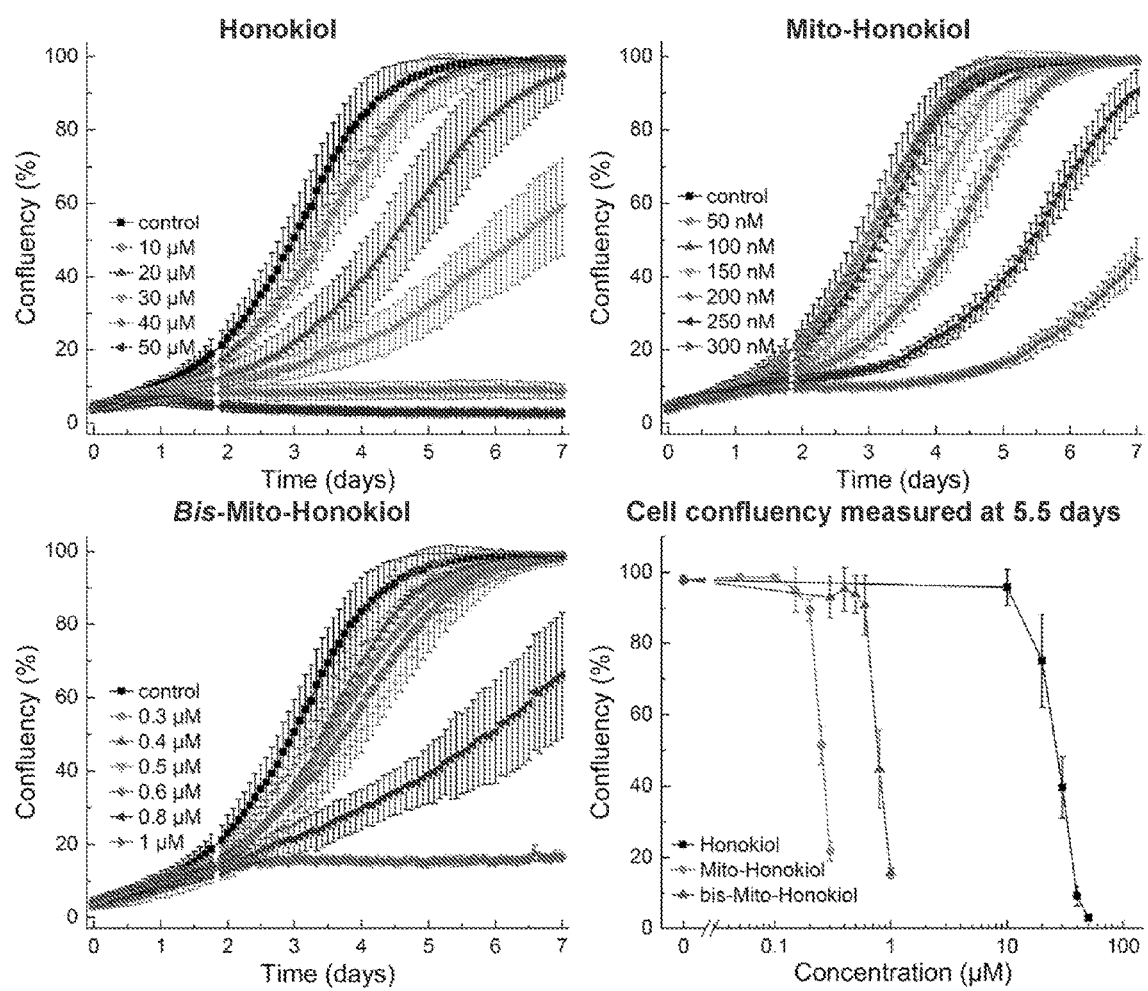
FIG. 2. Antiproliferative effects of honokiol and mito-honokiol. H2030 lung cancer cells were treated with micromolar levels of honokiol and nanomolar concentrations of mito-honokiol. Cell growth was continuously monitored. Changes in confluency were used as a surrogate marker of cell proliferation. After 5 days of incubation of H2030 cells with varying concentrations of honokiol and mito-honokiol, the confluency was plotted as a function of concentration.

In one embodiment, the present invention provides novel mito-honokiol compounds modified to selectively and synergistically inhibit cancer proliferation and progression. Specifically, the inventors have shown that linking triphenylphosphonium (TPP) to honokiol (and it's structural isomers, including magnolol) via long alkyl chains yields a novel mito-honokiol compound which is 100-1000 fold more potent than honokiol, while also exhibiting substantial inhibitory activity at nanomolar concentrations in vitro. The compound comprises mono- and bis-substituted mito-honokiol molecules (FIG. 1).

Methods of Synthesis.

The mito-honokiol compounds of the present invention are prepared by chemically linking triphenylphosphonium (TPP) to honokiol, via long alkyl chains.

Methods of Use.

In one embodiment, the invention provides a method of treating cancer in a subject comprising administering to the subject a therapeutically effective amount of a composition comprising at least one mito-honokiol compound of the present invention. In one embodiment, the composition comprises one mito-honokiol compound of the present invention, but in alternate embodiments, multiple mito-honokiol compounds of the invention may be administered.

In use, the mito-honokiol compounds of the present invention are more cytotoxic to cancer cells than to non-cancerous cells. The inventors have demonstrated that the mito-honokiol compounds of the present invention potently inhibit tumor cell proliferation and induce cytotoxicity by selectively inhibiting tumor, but not normal, cells.

The antiproliferative activity of the newly-synthesized honokiol analogs were tested using H2030 lung cancer cells and compared with the activity of the parent compound, honokiol (FIG. 1). The results indicate that substitution of honokiol with TPP increases the antiproliferative activity of the compound in vitro in the cellular model of lung cancer. Mitochondrial targeting of mito-honokiol led to improved antiproliferative activity at significantly lower doses (at least 100-fold) than required for the parent compound, honokiol.

Figure 3:
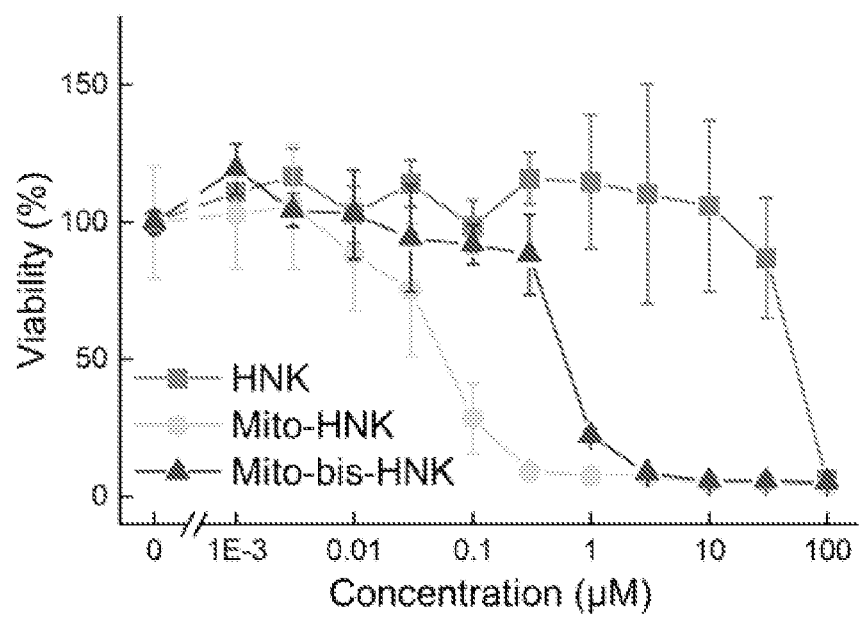
FIG. 3. Comparison of anti-proliferative effects of honokiol (HNK), mito-honokiol (Mito-HNK) and bis-mito-honokiol (Mito-bis-HNK) on human MiaPaCa-2 pancreatic cancer cells. The results indicate that substitution of honokiol with TPP significantly increases the antiproliferative activity of the compounds in an in vitro cellular model of pancreatic cancer. Mitochondrial targeting of honokiol leads to improved antiproliferative activity of honokiol at significantly lower doses (~1000-fold) than required for honokiol.

The inventors also compared the antiproliferative activity of mito-honokiol analogs to honokiol using human MiaPaCa-2 pancreatic cancer cells (FIG. 3). Their results indicate that substitution of honokiol with TPP significantly increases the antiproliferative activity of the compounds in a cellular model of pancreatic cancer. Results indicate that substitution of honokiol with triphenylphosphonium moiety (ies) significantly increases the antiproliferative activity of the compounds in cellular model of pancreatic cancer. Additionally, bis-mito-honokiol, a double substituted compound is also more potent than honokiol. Mitochondrial targeting of honokiol led to improved antiproliferative activity of honokiol at significantly lower doses (ca. 1000-fold) than required for the parent compound, honokiol. Ongoing studies indicated that aerosolized mito-honokiol inhibits lung cancer metastasis to the brain in an orthotopic model of lung cancer in mice.

The antiproliferative and antitumor mechanism of action of honokiols has been attributed by some to an effect on mitochondria that involves reactive oxygen species (inhibition or generation), or the antioxidant properties of honokiols. Interestingly, the inventors have found that, although the antioxidant properties of honokiols are removed by attachment of TPP (i.e., their mito-honokiols), the resulting compounds are still very potent inhibitors of proliferation. Thus, the mito-honokiols appear to target mitochondria selectively in tumor cells, and induce antiproliferative signaling events via a mechanism unrelated to conventional antioxidant mechanisms.

The invention also provides therapeutic compositions comprising at least one of the mito-honokiol compounds of the present invention and a pharmacologically acceptable excipient or carrier. The therapeutic composition may advantageously be soluble in an aqueous solution at a physiologically acceptable pH.

In one embodiment, the mito-honokiol compounds of the present invention provide effective methods of treating cancer. In one embodiment, the mito-honokiol compounds of the present invention potently inhibit tumor formation. In some embodiments, the cancer is a primary tumor. In some embodiments, the cancer is a metastatic cancer. In one embodiment, the mito-honokiol compounds of the present invention inhibit, reduce or prevent metastasis.

The term "metastasis," "metastatic tumor" or "secondary tumor" refers to cancer cells that have spread to a secondary site, e.g., outside of the primary tumor tissue. Secondary sites include, but are not limited to, the lymphatic system, skin, distant organs (e.g., liver, stomach, pancreas, brain, etc.) and the like. In some embodiments, the mito-honokiol compounds of the present invention provide methods of treating a primary or secondary tumor.

The compounds of the present invention also provide a neuroprotective effect to non-cancerous cells. Specifically, the mito-honokiol compounds of the present invention can be combined with existing treatments to protect non-cancerous cells in a subject.

Figure 4:
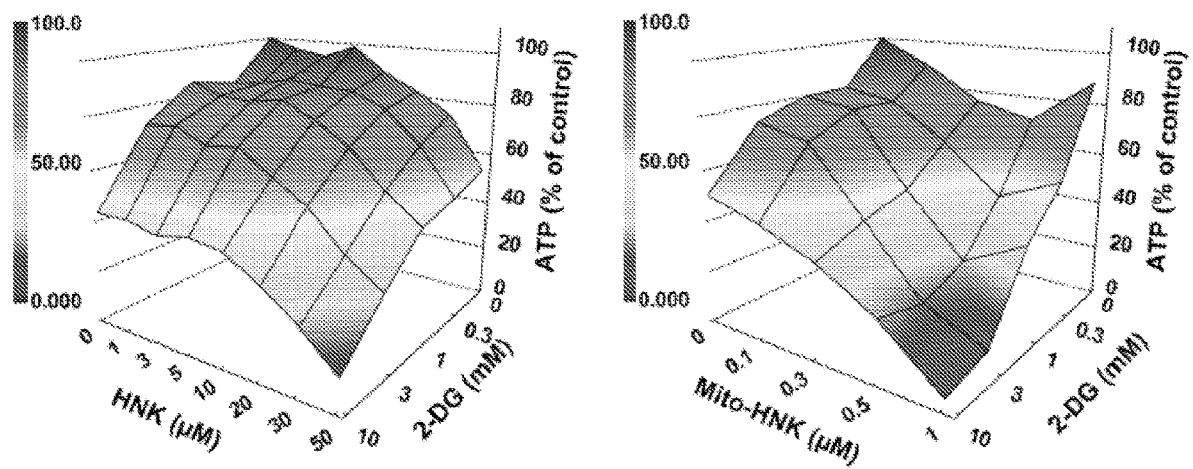
FIG. 4. Synergistic depletion of intracellular ATP in MiaPaCa-2 cells by combination of 2-deoxyglucose (2-DG) and honokiol (HNK) and mito-honokiol (Mito-HNK). The data were obtained on the human pancreatic cancer MiaPaCa-2 cell line. Honokiol and mito-honokiol synergize with the anti-glycolytic agent 2-deoxyglucose (2-DG) to cause a decrease in cellular ATP levels, however, mito-honokiol was needed at significantly lower concentrations than honokiol to deplete cellular ATP when combined 2-DG.
Figure 17A:
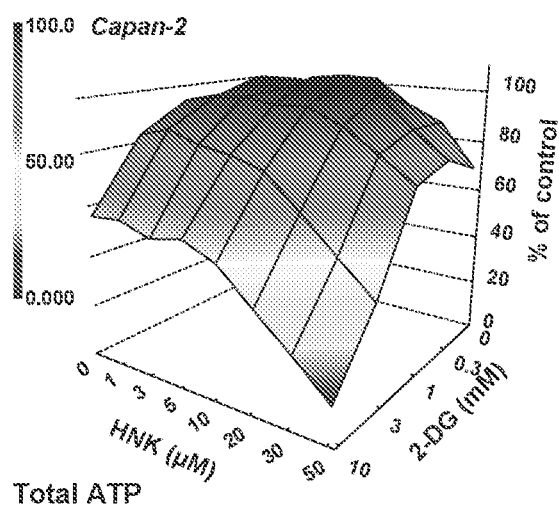
FIG. 17A-B. Effects of the combination of mito-honokiols with 2-deoxyglucose.
Figure 17B:
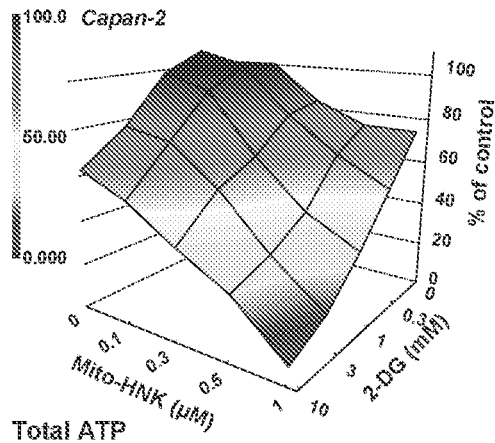

In one embodiment, the mito-honokiols of the present invention may be also used in combination with standard-of-care chemotherapeutics or with ionizing radiation to treat resistant cancer cells. Combining the mito-honokiols of the present invention with antiglycolytic agents (e.g. 2-deoxyglucose, 3-bromopyruvate) and other standard-of-care drugs (e.g. gemcitabine) on the rate of proliferation of pancreatic cancer cells, showed impressive results. Specifically, when tested on MiaPaCa-2 cell line (FIG. 4) both honokiol and mito-honokiol synergize with 2-deoxyglucose (2-DG) in decreasing cellular ATP levels. Notably, mito-honokiol was needed at significantly lower concentrations than honokiol to deplete cellular ATP, when combined with the antiglycolytic agent used. Similarly, treatment with mito-honokiol sensitized the low-glycolytic, 2-DG-resistant pancreatic cancer cell line, Capan-2, to 2-DG, resulting in a significant loss of cellular ATP (FIG. 17A-B).

By "tumor" we mean any abnormal proliferation of tissues, including solid and non-solid tumors. For instance, the composition and methods of the present invention can be utilized to treat cancers that manifest solid tumors such as pancreatic cancer, breast cancer, colon cancer, lung cancer, prostate cancer, thyroid cancer, ovarian cancer, skin cancer, and the like. The composition and methods of the present invention can also be utilized to treat non-solid tumor cancers such as non-Hodgkin's lymphoma, leukemia and the like.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex.

By "treating" we mean the management and care of a subject for the purpose of combating the disease, condition, or disorder. The terms embrace preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder. For example, treating cancer in a subject includes the reducing, repressing, delaying or preventing tumor growth, reduction of tumor volume, and/or preventing, repressing, delaying or reducing metastasis of the tumor. Treating cancer in a subject also includes the reduction of the number of tumor cells within the subject.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the mito-honokiol compounds of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the mito-honokiol compounds of the present invention is administered to a subject or is used in an assay or other method described herein or a cited reference, e.g., within about 1 hour of the administration or use of the mito-honokiol compounds of the present invention to about 3, 6, 9 months or more after a subject(s) has received the mito-honokiol compounds of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-honokiol compounds of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-honokiol compounds of the present invention is administered to a subject or is used in an assay or other method described herein or a cited reference, e.g., within about 1 hour of the administration or use of the mito-honokiol compounds of the present invention to about 3, 6, 9 months or more after a subject(s) has received the mito-honokiol compounds of the present invention.

By "administering" we mean any means for introducing the mito-honokiol compounds of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection. Another method of administration comprises oral gavage.

A preferred method of administering the mito-honokiol compounds or pharmaceutical compositions of the present invention for treatment of cancer, particularly lung cancer, is by aerosol. Another suitable method of administration is oral.

By "therapeutically effective amount" we mean an amount effective, at dosages and for periods of time necessary, to achieve the desired therapeutic result, such as reduction or reversal of angiogenesis in the case of cancers, or reduction or inhibition of T-cells in autoimmune diseases.

In one embodiment, the therapeutically effective amount ranges from between about 5-50 mg/kg. A therapeutically effective amount of the mito-honokiol compounds of the invention may vary according to factors such as the disease state, age, sex, and weight of the subject, and the ability of the mito-honokiol compounds to elicit a desired response in the subject. Dosage regimens may be adjusted to provide the optimum therapeutic response. A therapeutically effective amount is also one in which any toxic or detrimental effects of the mito-honokiol compounds of the present invention are outweighed by the therapeutically beneficial effects.

A "prophylactically effective amount" refers to an amount effective, at dosages and for periods of time necessary, to achieve the desired prophylactic result, such as preventing or inhibiting the rate of metastasis of a tumor. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

Kits.

In another embodiment, the present invention provides a kit comprising a pharmaceutical composition comprising the mito-honokiol compounds of the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1. Synthesis of Mito-Honokiol Compounds

The mito-honokiol compounds of the present invention are synthesized according to the following reaction:

Scheme 1. Synthesis of mito-honokiols.

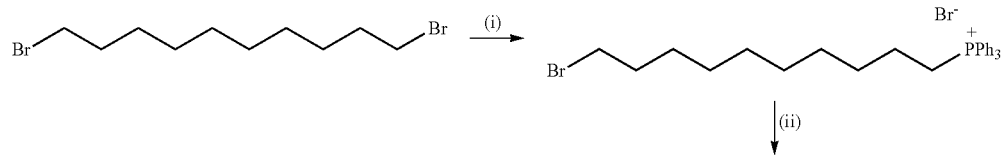

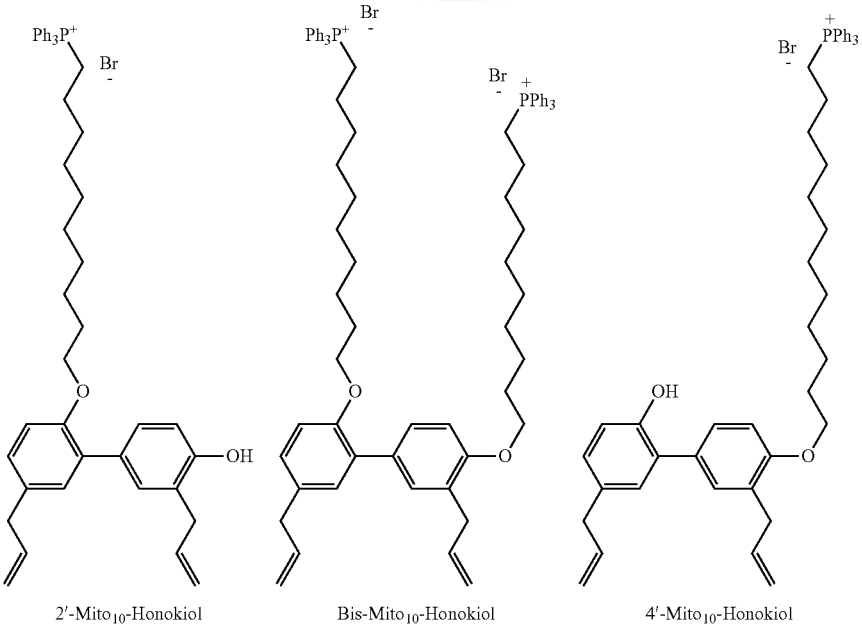

Reagents and conditions: (i) PPh₃, neat, 6 h, 90° C., 47%; (ii) Honokiol, K₂CO₃, DMF, 80%.

10-Bromodecyltriphenylphosphonium bromide 1

A mixture of triphenylphosphonium (1 g, 3.8 mmol) and dibromide (5.7 g, 19 mmol) was heated at 90° C. for 6 h. After cooling, the crude product was purified by flash chromatography (pentane, Et₂O and CH₂Cl₂/EtOH 9:1) to afford the corresponding phosphonium salt 1 as a white solid (1 g, 47% yield). $^{31}$P (400.13 MHz, CDCl₃) δ 24.32. $^1$H NMR (400.13 MHz, CDCl₃) δ 7.85-7.65 (15H, m), 3.73-3.66 (2H, m), 3.40-3.34 (2H, m), 1.80-1.75 (4H, m), 1.31-1.20 (12H, m).

Mito-Honokiol and Bis-Mito-Honokiol.

To a mixture of honokiol (0.27 g, 2.6 mmol), anhydrous potassium carbonate (0.28, 2 mmol) in DMF (4 mL) was added compound 1 (0.57, 1.0 mmol). The mixture was stirred at 30° C. for 6 h. The solvent was removed under vacuum and the residue was taken up into water and extracted with CH₂Cl₂. The organic layer was dried over Na₂SO₄, and the solvent was removed under reduced pressure. Purification by flash chromatography (Et₂O, CH₂Cl₂ and CH₂Cl₂/EtOH) delivered the corresponding Mito-Honokiols isomers (2, 3) and the Bis-Mito-Honokiol (4) as white solids (2, 3, 200 mg, % yield and 4, 50 mg, % yield). HRMS calculated for 2, 3 C₄₆H₅₂O₂P [MH]⁺667.3699, found, 667.3699. HRMS calculated for 4 C₇₄H₈₆O₂P₂ [MH]²⁺534.3046, found, 534.3044.

Mito-Honokiols 2, 3.

$^{31}$P (400.13 MHz, CDCl₃) δ 24.38, 24.28. $^1$H NMR (400.13 MHz, CDCl₃) δ 7.86-7.65 (15H, m), 7.35-6.95 (5H, m), 6.87 (1 h, 2d), J=8.3, 8.5), 6.06-5.86 (2H, m), 5.10-4.93 (4H, m), 3.98 (1H, t, J=3.9), 3.89 (1H, t, J=3.8), 3.80-3.70 (2H, m), 3.4-3.33 (4H, m), 1.77-1.30 (10H, m), 1.1-1.07 (6H, m).

Bis-Mito-Honokiol 4.

$^{31}$P (400.13 MHz, CDCl₃) δ 24.37. $^1$H NMR (400.13 MHz, CDCl₃) δ 7.88-7.70 (30H, m), 7.35-7.32 (2H, m), 7.12 (1H, d, J=1.7), 7.07 (1H, dd, J=8.3, 2.0), 6.88 (1H, d, J=8.3), 6.85 (1H, d, J=8.3), 6.05-5.85 (2H, m), 5.13-4.93 (4H, m), 3.97 (2H, t, J=6.3), 3.90 (2H, t, J=6.3), 3.85-3.73 (4H, m), 3.39 (2H, d, J=6.8), 3.36 (2H, d, J=6.5), 1.71-1.50 (10H, m), 1.20-1.33 (22H, m).

Example 2. Synthesis of

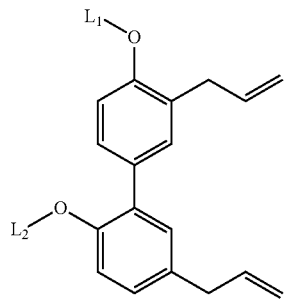

where L1 and/or L2 are comprised of organic linker attached to triphenylphosphonium moiety Synthetic Example

1.

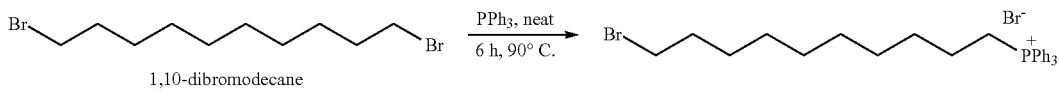

1,10-dibromodecane

2.
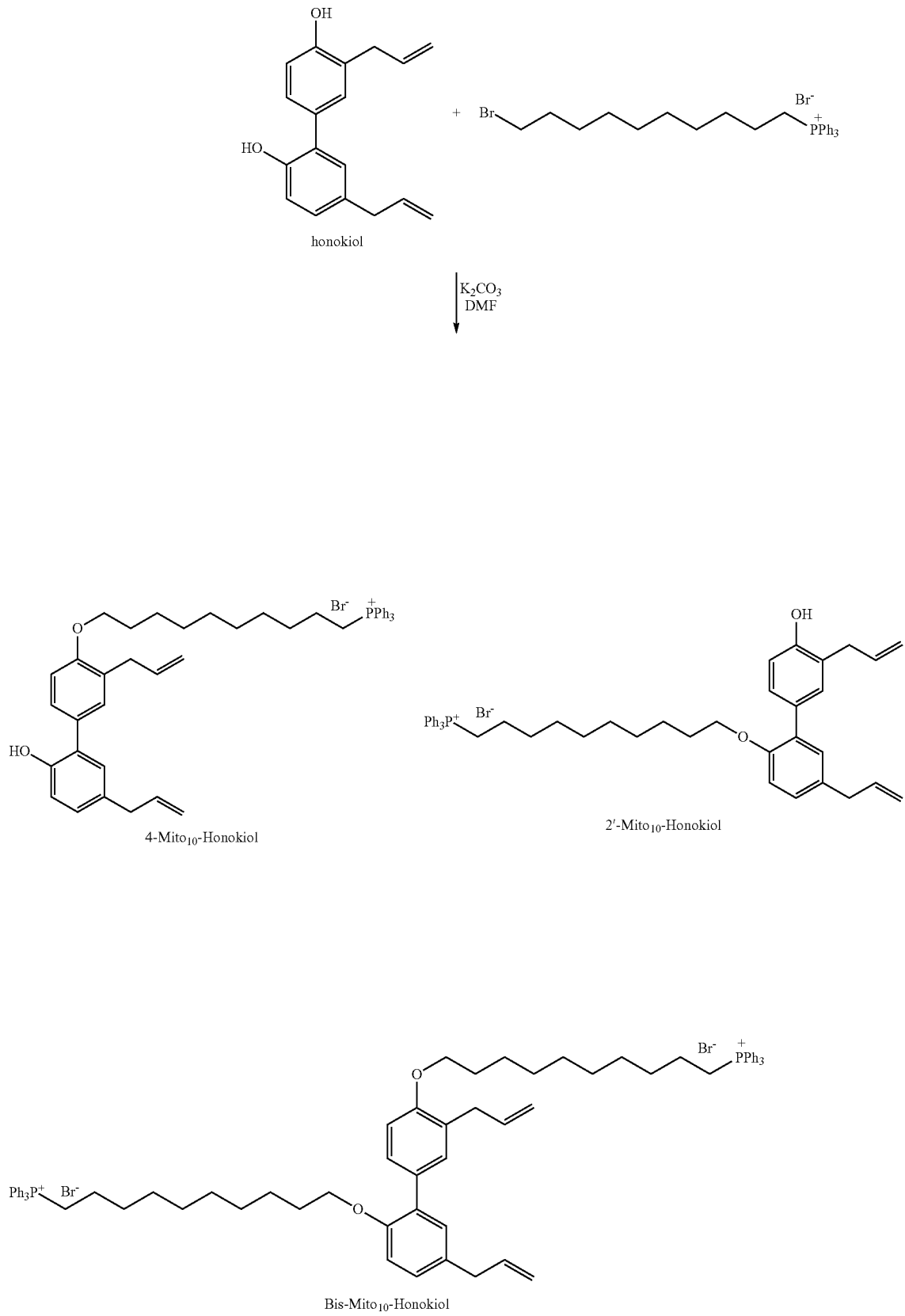

Example 3. Synthesis of
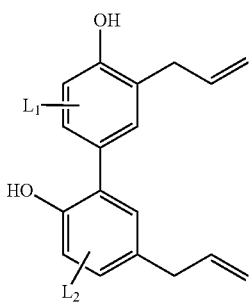
where L1 and/or L2 are comprised of organic linker attached to triphenylphosphonium moiety
Example 4. Synthesis of
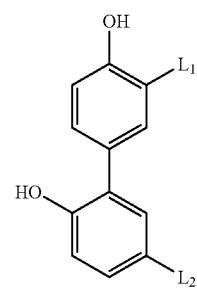
where L1 and/or L2 are comprised of organic linker attached to triphenylphosphonium moiety
Synthetic Example
1.
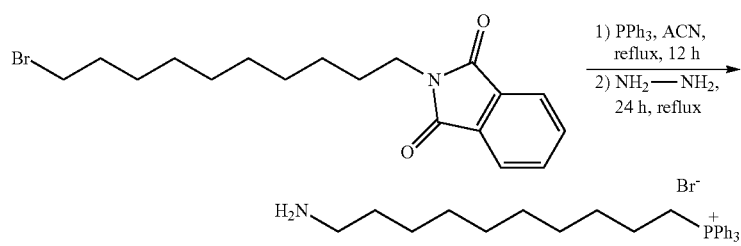
2.
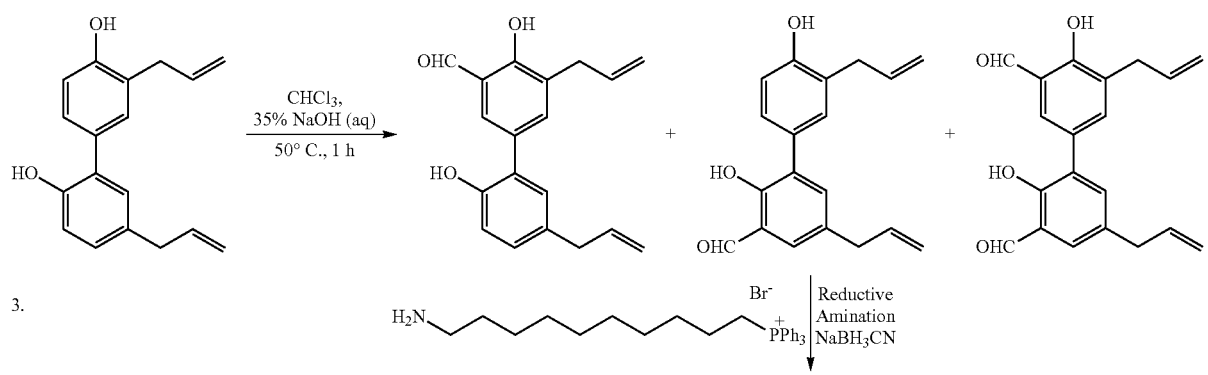
3.
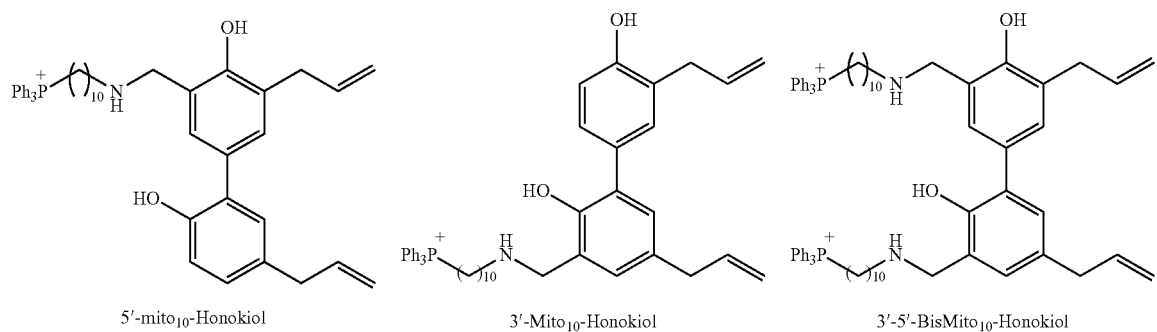
5′-mito$_{10}$-Honokiol     3′-Mito$_{10}$-Honokiol     3′-5′-BisMito$_{10}$-Honokiol Synthetic Example
1.
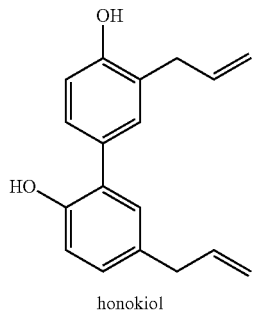
honokiol
→ Ac$_2$O, NaHCO$_3$, Ethyl acetate, 48 h →
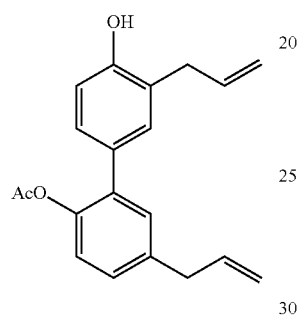
2.
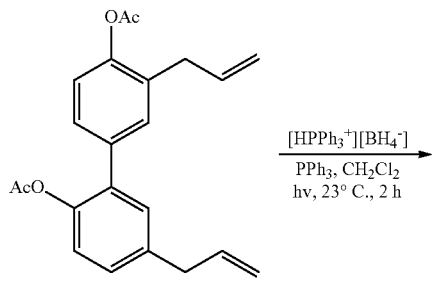
→ [HPPh$_3^+$][BH$_4^-$], PPh$_3$, CH$_2$Cl$_2$, hv, 23° C., 2 h →
→ NaOH, [Bu$_4$N$^+$][HSO$_4^-$], THF, r.t., 3 h →
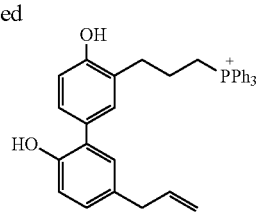
2-Mito$_3$-Honokiol
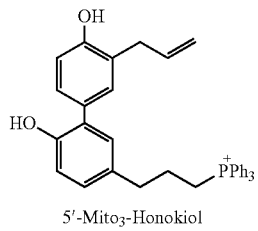
5′-Mito$_3$-Honokiol
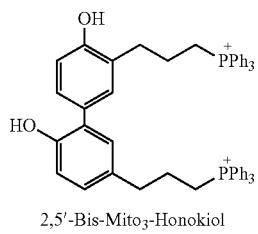
2,5′-Bis-Mito$_3$-Honokiol
Example 5. Synthesis of
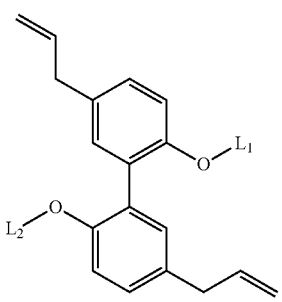
where L1 and/or L2 are comprised of organic linker attached to triphenylphosphonium moiety Synthetic Example
1.
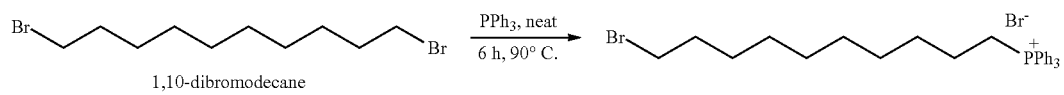
2.
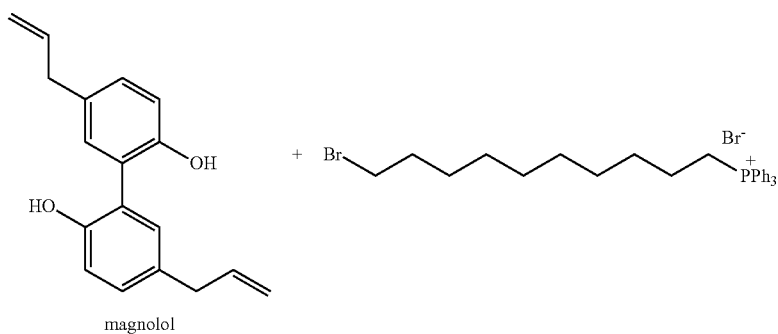
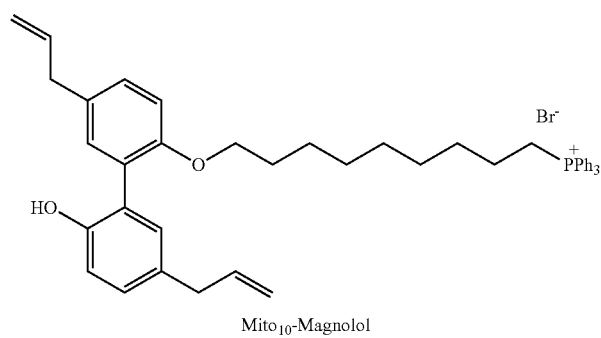
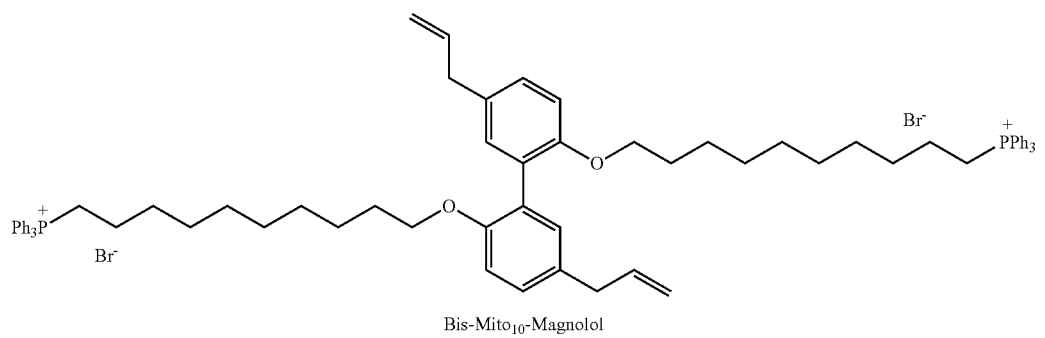

27
Example 6. Synthesis of
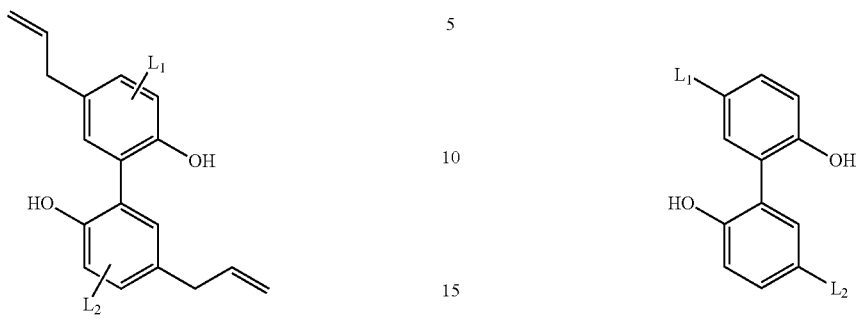
where L1 and/or L2 are comprised of organic linker attached to triphenylphosphonium moiety
Synthetic Example
28
Example 7. Synthesis of 5
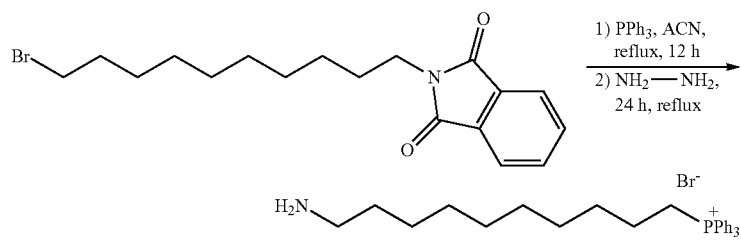
where L1 and/or L2 are comprised of organic linker attached to triphenylphosphonium moiety
1.
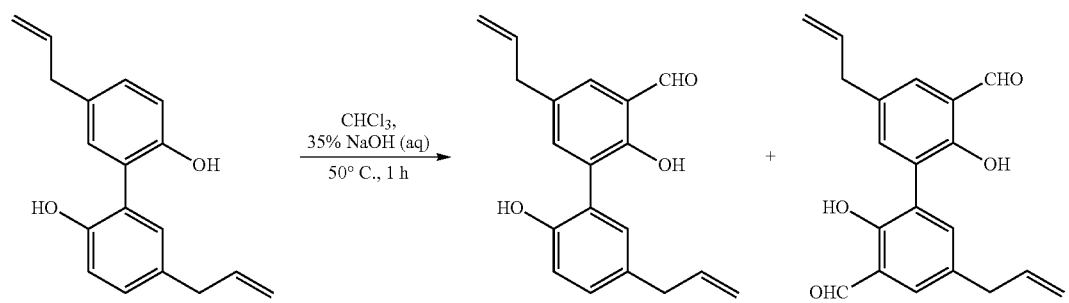
2.
3.
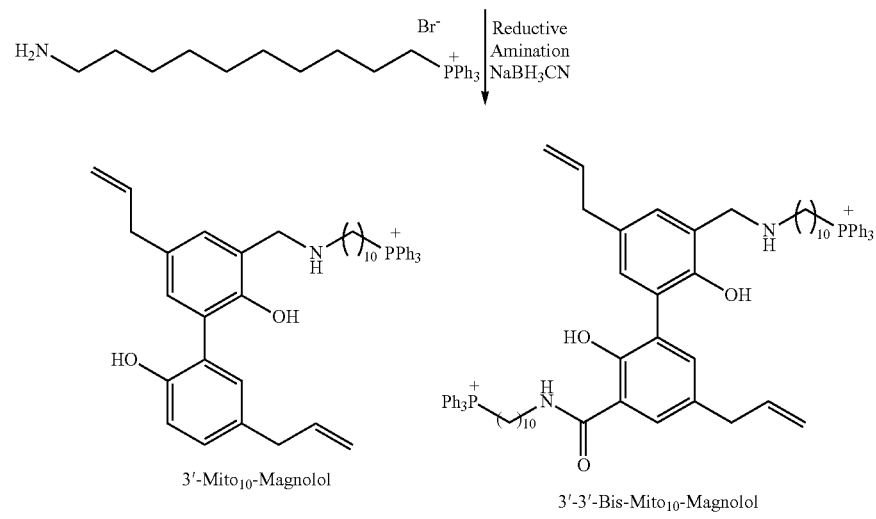
3'-Mito$_{10}$-Magnolol
3'-3'-Bis-Mito$_{10}$-Magnolol

Synthetic Example

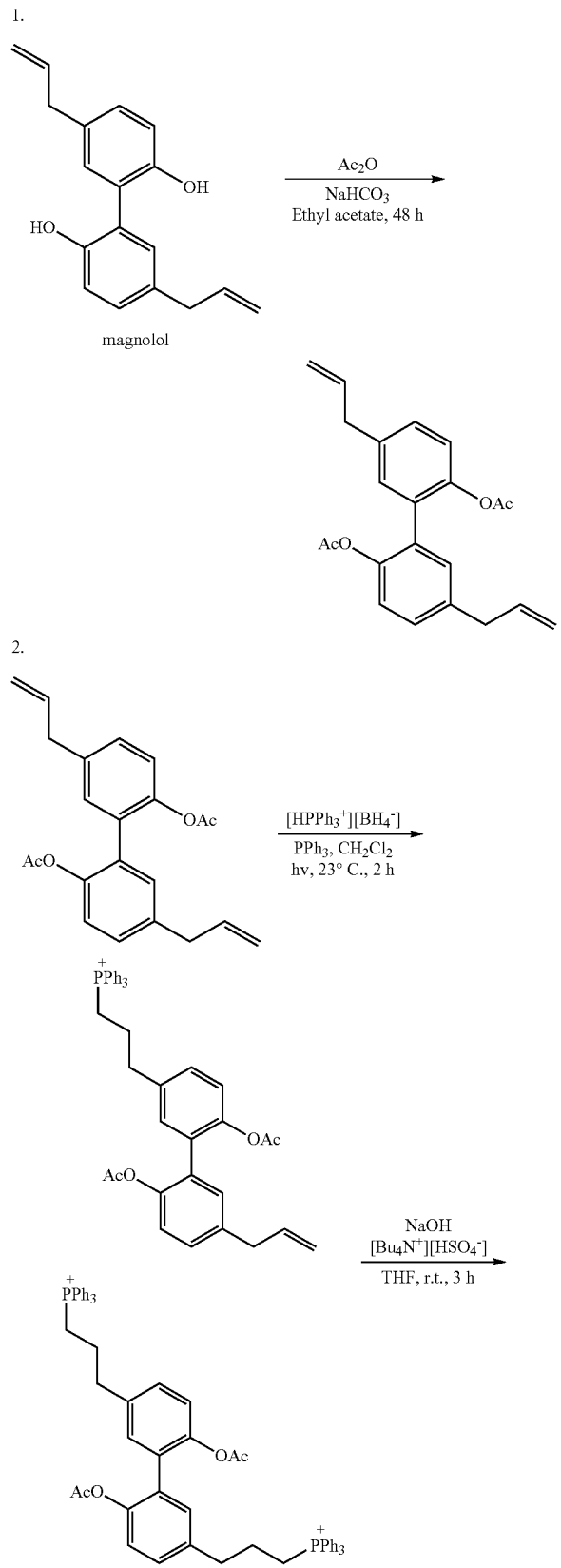

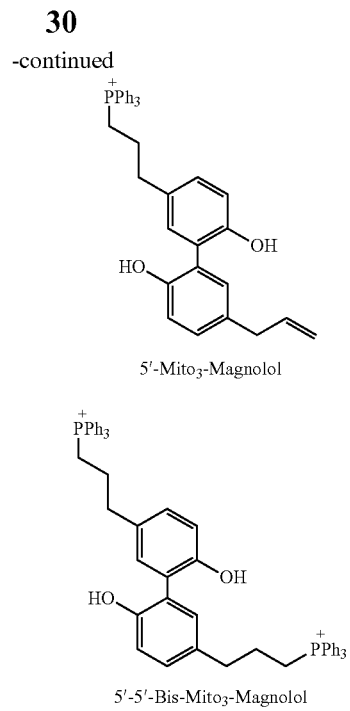

5'-Mito₃-Magnolol

5'-5'-Bis-Mito₃-Magnolol

Example 8. Use in Treatment of Cancer and Metastasis

Lung cancer is the leading cause of cancer death in the United States. Metastasis to lymph nodes (LN) and distal organs, especially the brain, leads to severe complications and is a major cause of death. Prevention of lung cancer development and metastases is an important strategy to reduce lung cancer mortality.

This Example demonstrates mitochondria-targeted HNK (Mito-HNK) is significantly more potent than HNK in the inhibition of lung cancer progression and lung cancer metastasis, specifically brain metastasis. The antimetastatic effects of Mito-HNK was evaluated in both LN and brain murine models of lung tumor metastasis. The H2030-BrM3 (Br-brain seeking) and DMS-273 lung tumor cells stably transfected with luciferase and green fluorescent protein were orthotopically injected into the lung for LN metastases, or directly injected into the left ventricle of the mouse for brain metastases. LN and brain metastases were monitored using a noninvasive bioluminescent in vivo imaging. Unless specified, Mito-HNK$_{10}$ (or Mito-HNK) relates to the mixture of the two isomers (2'-Mito-HNK and 4'-Mito-HNK).

The efficacy of Mito-HNK in preventing the migration of tumor cells to LN or the brain was tested by treating mice with Mito-HNK by aerosol (for the lung-to-LN metastasis model) or oral gavage starting the day after the tumor cell injection. Results revealed that Mito-HNK significantly prevented the metastasis of lung cancer cells to LN and the brain. We demonstrated that Mito-HNK decreased LN metastases incidence to 30%, compared with 100% in control mice, and inhibited brain metastasis nearly 70% compared with the control. Furthermore, analysis of Mito-HNK's mechanism of action, utilizing both RNA sequencing and a tyrosine kinase assay, suggests that its effect is mediated primarily by inhibiting the mitochondria complex I-STAT3 pathway. Mito-HNK specifically inhibits STAT3 phosphorylation regardless of EGFR (epidermal growth factor receptor) mutation status, and knockdown STAT3 abrogated both the antiproliferative and antimetastasis effects of Mito-HNK in brain metastatic and small lung cancer cells. These finding suggest that Mito-HNK could provide novel chemopreventive or therapeutic options for preventing both lung tumor progression and lung cancer metastasis.

Materials and Methods

Cell Culture and Reagents

Brain metastatic lung cancer cell lines PC9-BrM3 and H2030-BrM3 were generous gifts from Dr. Joan Massage (Memorial Sloan Kettering Cancer Center, New York, N.Y.). Small cell lung cancer cell line DMS-273 was purchased from Sigma-Aldrich (St. Louis, Mo.). Both PC9-BrM3 and H2030-BrM3 cell lines were maintained in RPMI-1640 medium (Gibco) supplemented with 10% fetal bovine serum, and DMS-273 cells were maintained in Waymouth's medium supplemented with 10% fetal bovine serum (FBS) (Invitrogen, Carlsbad, Calif.) and 2 mM glutamine (Fisher Scientific, Pittsburgh, Pa.) in a 37° C. humidified 5% CO2 incubator. Honokiol was purchased from Sigma-Aldrich (St. Louis, Mo.).

Cell Proliferation Assay

For the cell proliferation assay, cells were seeded onto 96-well tissue culture plates at 2-3,000 cells per well. Twenty-four hours after seeding, treatment group cells were exposed to various concentrations of HNK for 48 hours, and control group cells received fresh medium. The plate was incubated at 37° C. and 5% $CO_2$ and monitored in IncuCyte (Essen Bioscience, Ann Arbor, Mich.). Data analysis was conducted using IncuCyte 2011A software. All assays were performed in triplicate.

Transwell Invasion Assay

Boyden chamber transwells precoated with growth-factor-reduced Matrix were purchased from Fisher Scientific (Pittsburgh, Pa.). Transwell invasion assays were performed as described in the manufacture's protocol. Briefly, $2-3\times10^5$ cells were seeded into each transwell filled with serum-free RPMI-1640 media containing 10 μM HNK. Bottom wells were filled with RMPI-1640 media or Waymouth's medium with 10% FBS and either 10 μM or 20 μM HNK or 0.1 μM or 0.2 μM Mito-HNK. After 36 hours, cells were fixed with 10% formalin and stained with 5% crystal violet in 70% ethanol. Invaded cells were counted at a magnification of 10× in three randomly selected areas of each transwell, and the results were normalized to the control.

PathScan Receptor Tyrosine Kinase Assay

H2030-BrM3 and DMS-273 cells treated with control DMSO and various doses of HNK and Mito-HNK for four hours were lysed with 200 μL lysis buffer containing proteinase inhibitor cocktails (Cell Signaling Technology, Danvers, Mass.), sheared 10 times with a 28-gauge needle, spun at 16,000×g for 30 min, and normalized by protein concentration as determined by the Bradford method. Normalized lysate was resolved in a PathScan RTK Signaling Array, and the signaling array was examined by a Li-COR Odyssey infrared imaging system (Li-COR Biosciences-Biotechnology, Lincoln, Nebr.).

Western Blot Analysis

Cells were lysed with 200 μL of RIPA buffer containing proteinase inhibitor cocktails (Fisher Scientific, Pittsburgh, Pa.), sheared 10 times with a 28-gauge needle, spun at 16,000×g for 30 minutes, normalized by protein concentration as determined by the Bradford method, and boiled for 5 min. Normalized lysate was resolved by 4-12% sodium dodecyl sulfate polyacrylamide gel electrophoresis (SDS-PAGE) (Invitrogen, Carlsbad, Calif.) and immunoblotting with indicated antibodies. The following antibodies were used: p-EGFR (#3777S, Cell Signaling Technology, Danvers, Mass.), p-STAT3 (#9131S, 9134S, Cell Signaling Technology, Danvers, Mass.), p-AKT (#40605, Cell Signaling Technology, Danvers, Mass.), EGFR (4267S, Cell Signaling Technology, Danvers, Mass.), STAT3 (9139S, Cell Signaling Technology, Danvers, Mass.), AKT (92725, Cell Signaling Technology, Danvers, Mass.), Actin (SC-8432, Santa Cruz Biotechnology, Dallas, Tex.).

RNA Sequencing and Pathway Analysis

We conducted an RNA sequence study of human lung tumor metastases in mouse brains. Three brain metastases were sampled from mice not treated with HNK, and another three brain metastases were obtained from mice treated with HNK. Total RNA samples were extracted from these six samples using a Qiagen RNeasy Mini Kit. The quality of the total RNA samples obtained was very high, with RIN (RNA integrity number) values in the range of 9-10, and subjected to mRNA sequencing. We used a NEBNext Ultra RNA Library Prep Kit for Illumina to construct the RNA sequence libraries for these brain metastasis samples. The Agilent High Sensitivity DNA Chip analysis showed a narrow distribution (200-1000 bp) with a peak size of approximately 300 bp for the prepared RNA sequence library samples, indicating that they are of high quality for sequencing. A whole transcriptome analysis of these RNA-sequence library samples was performed using the HiSeq 2500 Sequencing platforms (Illumina, San Diego, Calif.). The experiment was single-end with a 50 nt read length. The qualities of the RNA sequence reads were analyzed using the FastQC program (http://www.bioinformatics.babraham.ac.uk/projects/fastqc/). Coverage for the samples ranged from 15 million-32 million reads per sample. The quality scores across all bases of the individual reads were at least >30, with an average around 37, and greatly exceeded the normal threshold of 20. In order to identify and unequivocally separate graft (human) and host (mouse) reads, processed sample reads were sequentially aligned to both graft (complete hg19 human genome [UCSC version, February 2009]) and host (complete mm9 mouse genome [UCSC version, July 2007]) genomes using Bowtie-TopHat (version 2.0.4, segment length 29 nt, one mismatch in segment permitted, for maximum sensitivity, coverage search performed) (Langmead et al., 2009; Trapnell et al., 2009). No deduplication was performed for post-assembly RNA-sequence analysis. Read counts were obtained using HTseq (Anders et al., 2015). Data normalization and differential expression analysis were performed using the statistical algorithms implemented in the EdgeR Bioconductor package (Robinson et al., 2010). False discovery rate (FDR)-corrected p-values of less than 0.05 were used as criteria for significantly regulated genes. In addition, both metastatic tumors (human) and stroma (mouse) cells were used to identify key gene expression patterns in response to HNK using the species-specific RNA-sequence approach. We used a strategy that efficiently separates human lung tumor sequence data from that of xenograft mice (mice with genetically human tumors) into separate microenvironment and tumor expression profiles (Bradford et al., 2013; Rossello et al., 2013). Using this tool, we obtained more-accurate RNA expression profiles for both metastatic human lung tumors and mouse stromal cells.

Endogenous STAT3 Knockdown

Lentiviral particles against STAT3 were purchased from Santa Cruz Biotechnology, Inc. (Dallas, Tex.). Lentiviral particles were infected in PC9-BrM3, H2030-BrM3, and DMS-273 in the presence of 8 μg/mL polybrene, and infected cells were selected with puromycin (2 µg/ml) for three days to obtain stable knockdown cells.

Brain Metastases in Mouse Model Via Ultrasound-Guided Left Ventricle Injection Technique Animal procedures were performed in accordance with the Medical College of Wisconsin Institutional Animal Care and Use Committee. For the lung cancer brain metastasis study, four-six-week-old, female, nonobese-diabetic-background (NOD/SCID) mice were used. 2×105 brain-seeking cells, H2030-BrM3, were suspended in 0.1 ml PBS and injected into the left ventricle under ultrasound guide (ECHO 707, GE, Milwaukee, Wis.). One day after engrafting H2030-BrM3 cells in arterial circulation, mice were randomly grouped into the vehicle treatment group or the HNK treatment group (10 mg/kg body weight). Mice were treated with either solvent control (0.1% DMSO in coin oil) or HNK by oral gavage for four weeks; during this time, metastases were monitored by bioluminescence with an Xenogen IVIS-200 (Alameda, Calif.) alone at treatment time, and were confirmed with ex vivo luminescence, ex vivo green fluorescent protein (GFP) fluorescence, and haematoxylin and eosin (H&E) and GFP staining at the endpoint.

For the lung tumor lymph nodes metastasis study, $10^4$ cells were resuspended in a 1:2 mixture of PBS and growth factor reduced Matrigel (BD Biosciences, San Jose, Calif.) and then injected into the lung. HNK treatment was started one day post orthotopical injection of tumor cells via aerosol delivery.

In Vivo Orthotopic Lung Cancer Mouse Model

We used an orthotopic model of lung adenocarcinoma cells (H2030-BrM3 cells) in nude mice to evaluate the inhibitory effect of aerosolized HNK on lung tumor growth and lymph node metastasis. Five-week-old male athymic nude mice were used for experiments. Mice were anesthetized with isoflurane and placed in the right lateral decubitus position. A total of $1\times10^6$ H2030-BrM3 cells in 50 µg of growth factor reduced Matrigel (BD Biosciences, San Jose, Calif.) in 50 µL of RPMI-1640 medium were injected through the left rib cages of mice into their left lungs, as previously described (Nguyen et al., 2009). One week after the injections, mice in the HNK group were treated with 5 mg/ml aerosolized HNK once a day, five days a week, for four weeks. Tumor growth and metastases phenotypes were monitored during this time by bioluminescence with an Xenogen IVIS-200. Mice were sacrificed at the endpoint; tissues were extracted, freshly frozen, and OCT-fixed or formalin-fixed with 10% zinc for later western blot and immunohistochemistry (IHC) analyses.

In Vivo Imaging System

An in vivo imaging system (IVIS) consists of a highly sensitive, charge-coupled digital camera with accompanying advanced computer software for image data acquisition and analysis. This system captures photons of light emitted by reagents or cells that have been coupled or engineered to produce bioluminescence in the living animal. The substrate luciferin was injected into the intraperitoneal cavity at a dose of 150 mg/kg body weight (30 mg/ml luciferin) approximately 10 minutes before imaging. Mice were anesthetized with isoflurane/oxygen and placed on the imaging stage. Photons emitted from the lung region were quantified using Living Image software (Xenogen Corporation, Alameda, Calif.).

Histopathology Analysis

Mouse brains were fixed in a 10% zinc formalin solution overnight and stored in 70% ethanol for histopathology evaluation. Serial tissue sections (5 µm each) were made and stained with H&E or GFP and examined histologically under a light microscope to assess the severity of the tumor development.

Statistical Analysis

A two-tailed Student's T-test was used to evaluate the differences between the control samples and the treated samples. *$P<0.05$ and **$P<0.005$ were considered statistically significant.

Results

Inhibition of Mitochondrial Complex I Activity

Figure 5A:
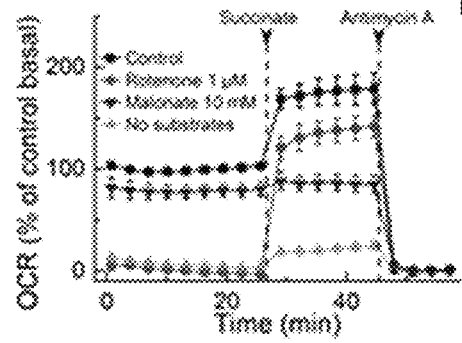
FIG. 5A-D. Inhibition of mitochondrial complex I activity by mito-honokiol. Cells were pretreated for 24 h with Mito-HNK and HNK, cell-membrane was permeabilized, and OCR measured upon addition of mitochondrial substrates/inhibitors. (A, C) show OCR changes in the control and in rotenone- and malonate-treated permeabilized cells. Rotenone (a complex I inhibitor) greatly diminished OCR that was restored by added succinate. In the presence of malonate (a complex II inhibitor) that did not significantly affect complex I-mediated OCR, the addition of succinate did not stimulate OCR and the addition of antimycin A decreased both pyruvate- and succinate-induced OCR. Both HNK and Mito-HNK inhibit complex I in both H2030-BrM3n (B) and DMS-273 (D) cells.
Figure 5B:
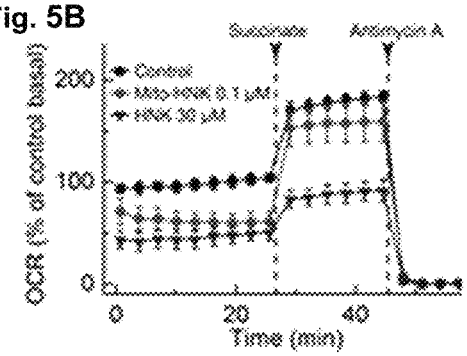
Figure 5C:
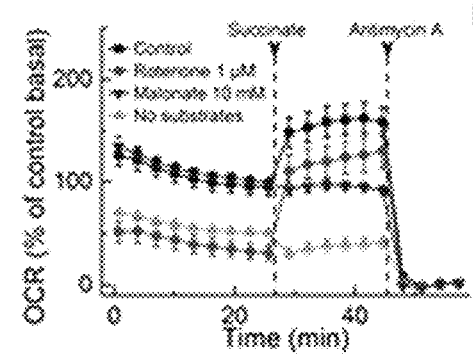
Figure 5D:
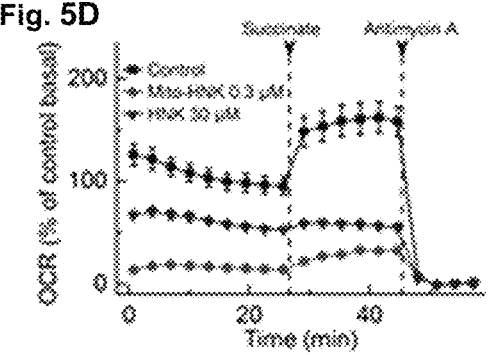

Mito-HNK is designed to target mitochondria, so we examined the specificity of Mito-HNK in the inhibition of mitochondrial function and cellular respiration. We previously published that HNK inhibited squamous lung cancer progression by at least partially targeting mitochondria. Results indicate that Mito-HNK inhibits cellular respiration (or OCR) and mitochondrial function at a concentration more than 100-fold lower than HNK in intact H2030-BrM3 brain metastatic lung cancer cells (FIGS. 5A and 5B) and highly invasive DMS-273 small cell lung cancer cells (FIGS. 5C and 5D). Both the basal respiration and the response to mitochondrial stressors (oligomycin, dinitrophenol) were diminished by Mito-HNK (not shown). To investigate the mechanism of inhibition of mitochondrial function, we measured the activity of mitochondrial complexes in response to HNK and Mito-HNK. We pretreated cells with Mito-HNK and HNK for 24 h, permeabilized their cell membranes, and measured their OCR upon the addition of mitochondrial substrates/inhibitors. This approach has many advantages, including high throughput, the lack of requirement of cell fractionation, and the possibility of monitoring the effect on two mitochondrial complexes in a single run. FIGS. 5A and 5C show OCR changes in control and rotenone- and malonate-treated permeabilized cells. Rotenone (a complex I inhibitor) greatly diminished the OCR that was restored by added succinate. In the presence of malonate (a complex II inhibitor) that did not significantly affect complex I-mediated OCR, the addition of succinate did not stimulate OCR and the addition of antimycin A decreased both pyruvate- and succinate-induced OCR (FIGS. 5A and 5C). These studies established the optimal use of permeabilized cells for bioenergetics function assays (Salabei J K, Gibb A A, Hill B G. Comprehensive measurement of respiratory activity in permeabilized cells using extracellular flux analysis. Nat Protoc. 2014; 9(2):421-38).

Figure 6:
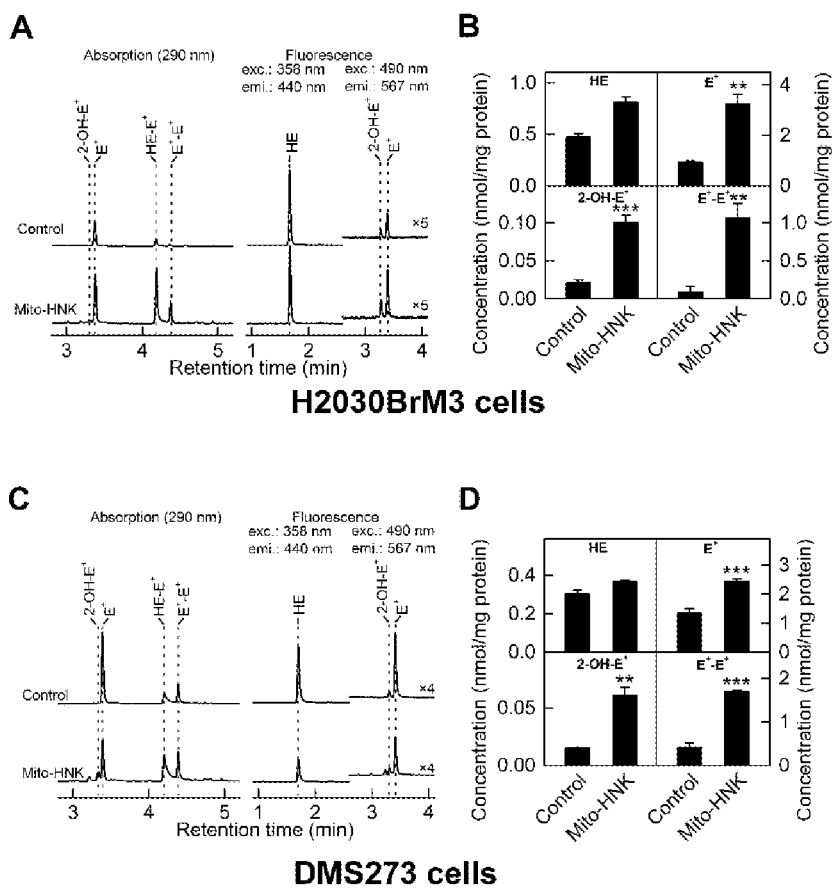
FIG. 6A-D. Production of superoxide ($O_2^{\cdot-}$) and other oxidants by mito-honokiol. The effect of Mito-HNK on cellular ROS production, as measured by HPLC-based analyses of the oxidation of the HE probe. (A, C) HPLC traces recorded; (B, D) quantitative analyses of the products of HE oxidation. $p<0.01$, *$p<0.001$ in both H2030BrM3 (A,B) and DMS273 (C,D) cells.

Effects of Mito-Honokiol in Production of Superoxide ($O_2^{\bullet-}$) and Mitochondrial Peroxiredoxin-3 Oxidation Many factors may be responsible for the Mito-HNK-induced activation of AMPK, one of the proposed mechanisms involving ROS generation (Hwang A B, Ryu E A, Artan M, Chang H W, Kabir M H, Nam H J, et al. Feedback regulation via AMPK and HIF-1 mediates ROS-dependent longevity in *Caenorhabditis elegans*. Proc Natl Acad Sci USA. 2014; 111(42)). We have shown that HNK induces mitochondrial ROS production (Pan J, Zhang Q, Liu Q, Komas S M, Kalyanaraman B, Lubet R A, et al. Honokiol inhibits lung tumorigenesis through inhibition of mitochondrial function. Cancer Prev Res (Phila). 2014; 7(11):1149-59). Because Mito-HNK is more potent than HNK in complex I inhibition (FIG. 5), we hypothesized that Mito-HNK would significantly increase ROS levels in lung cancer cells. Preliminary data show that Mito-HNK induces ROS formation in H2030-BrM3 cells. 2-OH-E$^+$, the $O_2^{\bullet-}$-specific product of hydroethidine (HE) oxidation, was increased in Mito-HNK (1 µM)-treated H2030-BrM3 and DMS-723 cells (FIG. 6). A strong induction of one-electron oxidation of HE with the formation of diethidium (E$^+$-E$^+$) also was observed, indicating that Mito-HNK induces generation of another, stronger oxidant in both H2030-BrM3 and DMS-273 cells (FIG. 7). To determine the possible direct targets of ROS stimulated upon inhibition of the mitochondrial complex I, we tested the oxidation status of cytosolic (Prx1) and mitochondrial (Prx3) peroxiredoxins. Results indicate that 24-h treatment of H2030-BrM3 and DMS-273 cells with Mito-HNK (0.2 and 0.4 µM, respectively) leads to significant oxidation of mitochondrial Prx3 with relatively a small extent of oxidation of cytosolic Prx1 (FIG. 7). This is consistent with Mito-HNK-induced mitochondrial ROS formation, with possible diffusion of a fraction of $O_2^{\cdot-}$ and/or $H_2O_2$ into the cytosol.

Figure 8A:
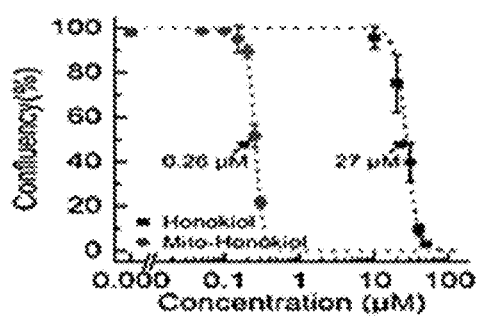
FIG. 8A-D. Mito-honokiol exhibits inhibitory effects on lung cancer proliferation and invasion at submicromolar concentrations. Effects of Mito-HNK on the inhibition of lung cancer cells proliferation and invasion were examined in H2030-BrM3 NSCLC (A) and DMS-273 SCLC (B) cell lines. (A-B) H2030-BrM3 or DMS-273 cells were treated with control DMSO, various doses of HNK, or Mito-HNK for 24 hours, and cell proliferation was monitored with an IncuCyte Live imaging system. Mito-HNK significantly inhibited both H2030-BrM3 and DMS-273 cell proliferation in a dose-dependent manner, and Mito-HNK was more than 100-fold more potent than HNK in suppressing the proliferation of both H2030-BrM3 and DMS-273 SCLC cells. (C) Anti-invasive effects of Mito-HNK were examined via Boyden chamber invasion assay in H2030-BrM3 and DMS-273 cells. (D) Quantification of the invasion assay in H2030-BrM3 and DMS-273 treated with either control DMSO, HNK, or Mito-HNK indicate that Mito-HNK is about 100-fold more potent in the inhibition of lung cancer cells invasion.
Figure 8B:
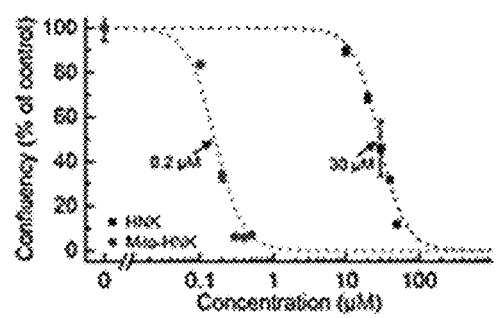
Figure 8C:
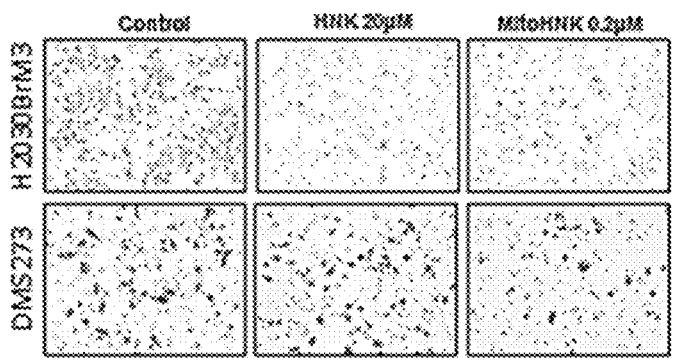
Figure 8D:
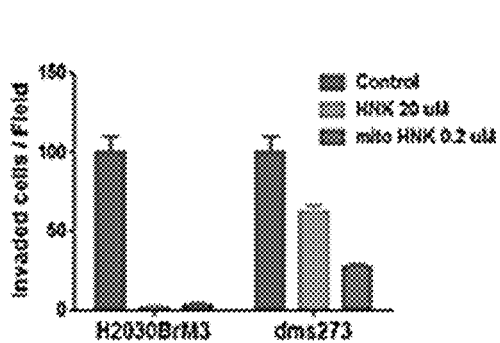

Mito-HNK Exhibits Sub-Micromole Potency on Lung Cancer Proliferation and Invasion Next, we examined the anticancer effects of Mito-HNK compared to HNK in vitro. Various doses of HNK and Mito-HNK were treated in either H2030-BrM3 or DMS-273 cells, and the antiproliferative effects were monitored with an IncuCyte Live-Cell Imaging Analyzer. Both HNK and Mito-HNK show antiproliferative effects in H2030-BrM3 and DMS-273, as shown in FIGS. 8A and 8B, respectively. Interestingly, Mito-HNK inhibits cell proliferation at significantly lower doses than HNK with the IC50 values of 0.26 and 27 µM for H2030-BrM3 and 0.2 and 30 µM for DMS-273, respectively. Furthermore, we examined the anti-invasive effects of Mito-HNK in H2030-BrM3 and DMS-273 cells via a Boyden chamber invasion assay. Both cells were treated with vehicle control (DMSO), HNK (20 µM), and Mito-HNK (0.2 µM) for 36 hours, and invaded cells were determined. As shown in FIG. 8C, H2030-BrM3 and DMS-273 cells treated with both HNK and Mito-HNK have significantly fewer invasive cells than the vehicle-control-treated cells (FIGS. 8C and 8D). Antiproliferative (FIGS. 8A and 8B) and anti-invasive effects (FIGS. 8C and 8D) of MitoHNK in vitro demonstrated nearly a 100-fold increase in antiproliferative and anti-invasive potency by targeting HNK to mitochondria.

Figure 9A:
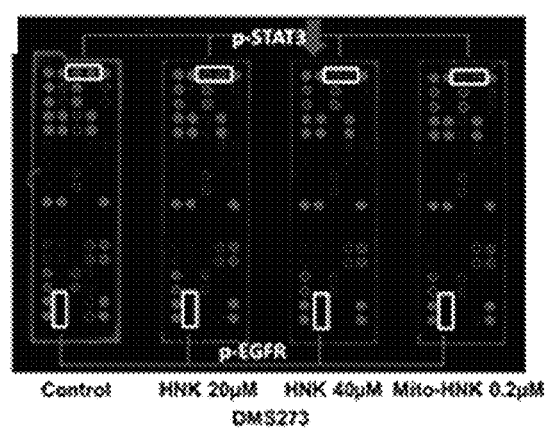
FIG. 9A-E. Role of STAT3 in mediating mito-honokiol's anti-cancer effects. (A) The PathScan receptor tyrosine kinase assay indicated that Mito-HNK inhibits STAT3 phosphorylation levels without affecting EGFR phosphorylation in DMS-273 cell line. (B) Effects of Mito-HNK in STAT3 phosphorylation were further validated via a Western blot assay. Both cytoplasmic and mitochondrial STAT3 phosphorylation were downregulated by Mito-HNK in both DMS-273 and H446 cell lines. (C) Knock down of endogenous STAT3 gene via the shRNA approach was confirmed by a Western blot analysis. (D) The STAT3 knockdown in DMS-273 cells significantly inhibits the proliferation of DMS-273 cells and abrogated the antiproliferative effects of both HNK and Mito-HNK. (E) Mito-HNK does not show significant inhibitory effects on the proliferation of NHBE (normal lung epithelial cells) compared to DMS-273 SCLC cells.
Figure 9B:
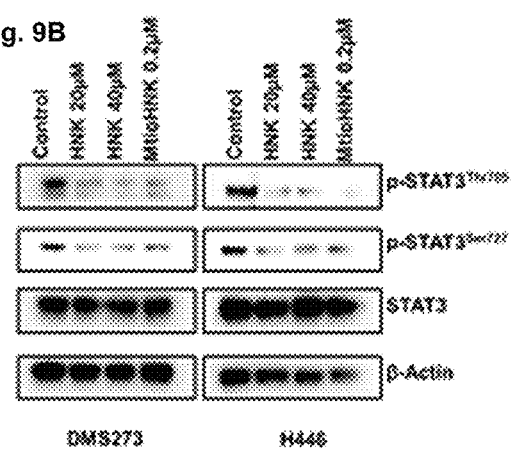

STAT3-Mitochondrial Complex I as Potential Target of Mito-HNK in the Inhibition of Lung Cancer Brain Metastasis Our results demonstrated the effects of Mito-HNK on the inhibition of lung cancer brain metastasis, but we wanted to look at the molecular mechanism of action behind the effects of Mito-HNK. We examined the potential mechanisms of Mito-HNK action on the inhibition of both brain metastatic lung cancer cell and SCLC cell progression via a PathScan receptor tyrosine kinases (RTK) assay (FIG. 9A), which has been used extensively to study mechanisms of action of candidate drugs (Vazquez-Martin et al., 2013). The PathScan RTK signaling array allows the examination of 28 different tyrosine kinase receptors as well as 11 downstream signaling nodes that frequently are deregulated in many types of cancer, including lung cancers. For the RTK signaling array, we treated DMS-273 cells with two different doses of HNK (10 µM and 20 µM) and Mito-HNK (0.2 µM) for six hours. The PathScan RTK signaling array results revealed that both HNK and Mito-HNK treatments dramatically decreased STAT3 phosphorylation levels compared to that of vehicle-control-treated cells (FIG. 9A), suggesting that STAT3 could be the major downstream target of Mito-HNK. We also observed similar pattern in H2030-BrM3 cells treated with HNK or Mito-HNK (Sup FIG. 9A). Then, we further validated the effects of HNK and Mito-HNK on STAT3 phosphorylation in DMS-273 cells via a Western blot analysis (FIG. 9B). Both cytoplamic and mitochondrial STAT3 phosphorylation was significantly inhibited by Mito-HNK (FIG. 9B). Previously, HNK was reported to be effective in the treatment of head and neck squamous cell carcinoma by targeting the EGFR signaling pathway (Park et al., 2009). However, we observed that HNK only targets EGFR phosphorylation in the PC9-BrM3 cell line that harbors the EGFR mutation but not in the H2030-BrM3 that harbors the KRAS mutation (data not shown). Therefore, the effects of HNK on the EGFR signaling pathway could be in a manner specific to cell type, tissue, or driver mutation. Mito-HNK-inhibited STAT3 phosphorylation in PC9-BrM3 (EGFR mutation), H2030-BrM3 (KRas mutation), and DMS-273 (both EGFR and KRas wild type) regardless of the driver mutation status, suggesting that STAT3 could be a universal target of HNK via multiple receptor tyrosine kinases regardless of driver mutations in lung cancers.

Figure 9C:
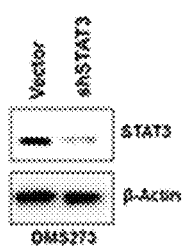
Figure 9D:
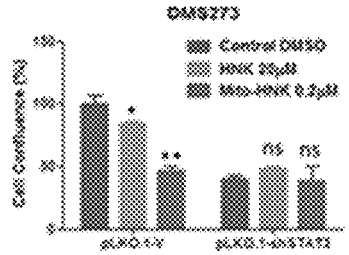

Next, we validated the role of STAT in mediating anticancer effects of Mito-HNK in lung cancer cells. We used the shRNA approach to knock down endogenous STAT3 expression levels (FIG. 9C) and tested if the STAT3 knockdown decreased the anticancer effects of Mito-HNK. We found that the STAT3 knockdown significantly decreased the proliferation rate of DMS-273 cells compared to vector control infected cells (FIG. 9D). In addition, the fact that the STAT3 knockdown abrogated the antiproliferative effect of Mito-HNK in DMS-273 cells at the dose and time we tested indicates that STAT3 plays a significant role in mediating the anticancer effects of Mito-HNK.

Figure 9E:
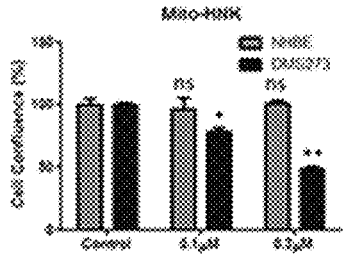

We examined the toxicity of Mito-HNK in NHBE (normal lung epithelial cells) and confirmed that Mito-HNK has minimal toxic effects in normal lung cells, whereas it has great cytotoxic effects in lung cancer cells (FIG. 9E).

Mito-HNK Overcomes EGFR TKI Resistance in Lung Cancer

Figure 10:
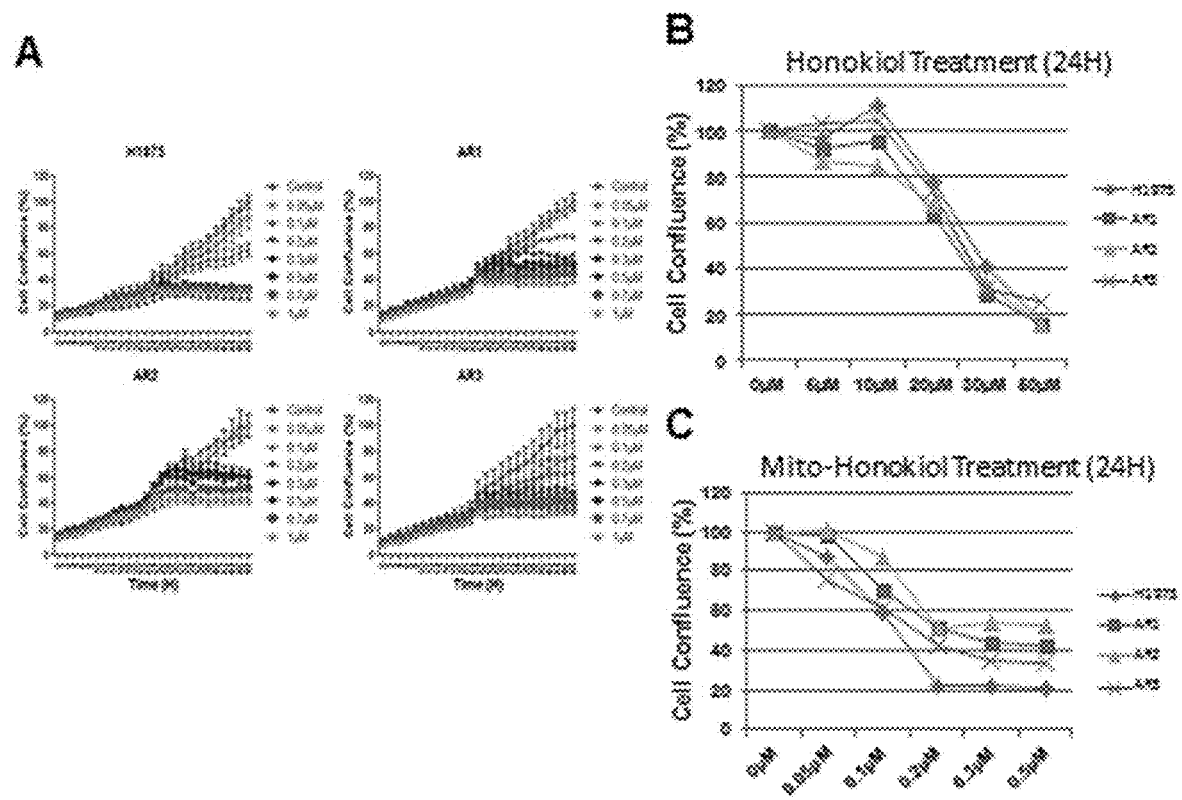
FIG. 10A-C. Effects of mito-honokiol in EGFR TKI drug-resistant lung cancer cells. (A) Effects of Mito-HNK in EGFR TKI drug-resistant lung cancer cells, AR1, AR2, and AR3, and EGFR TKI drug-sensitive lung cancer cells H1975 were examined. Mito-HNK significantly inhibits the proliferation of both EGFR TKI drug-sensitive and EGFR TKI drug-resistant lung cancer cells compared to cells treated with control DMSO. (B) Both EGFR TKI drug-sensitive and EGFR TKI drug-resistant lung cancer cells were sensitive to HNK and Mito-HNK, but Mito-HNK showed about 100-fold potency in the inhibition of both EGFR TKI drug-sensitive and EGFR TKI drug-resistant lung cancer cell lines.

Mitochondrial ROS and STAT3 have been demonstrated to play a critical role in mediating cancer drug resistance in many types of cancers ((Alas and Bonavida, 2003; Bewry et al., 2008; Lee et al., 2014; Li et al., 2016; Nair et al., 2012; Yu et al., 2015). Therefore, we examined if Mito-HNK has an anticancer effect in afatinib, the EGFR TKI drug-resistant lung cancer cell lines (AR1, AR2, and AR3) that we previously developed (Lee et al., 2016). As shown in FIG. 10, both afatinib-sensitive H1975 cells and afatinib-resistant AR1, AR2, and AR3 cells were sensitive to HNK (FIG. 10B) and Mito-HNK (FIG. 10 A,C), with Mito-HNK showing efficiency at submicromolar concentrations.

Mito-HNK Exhibits AntiCancer Effects in Orthotopic Lung Cancer Model In Vivo

Figure 11:
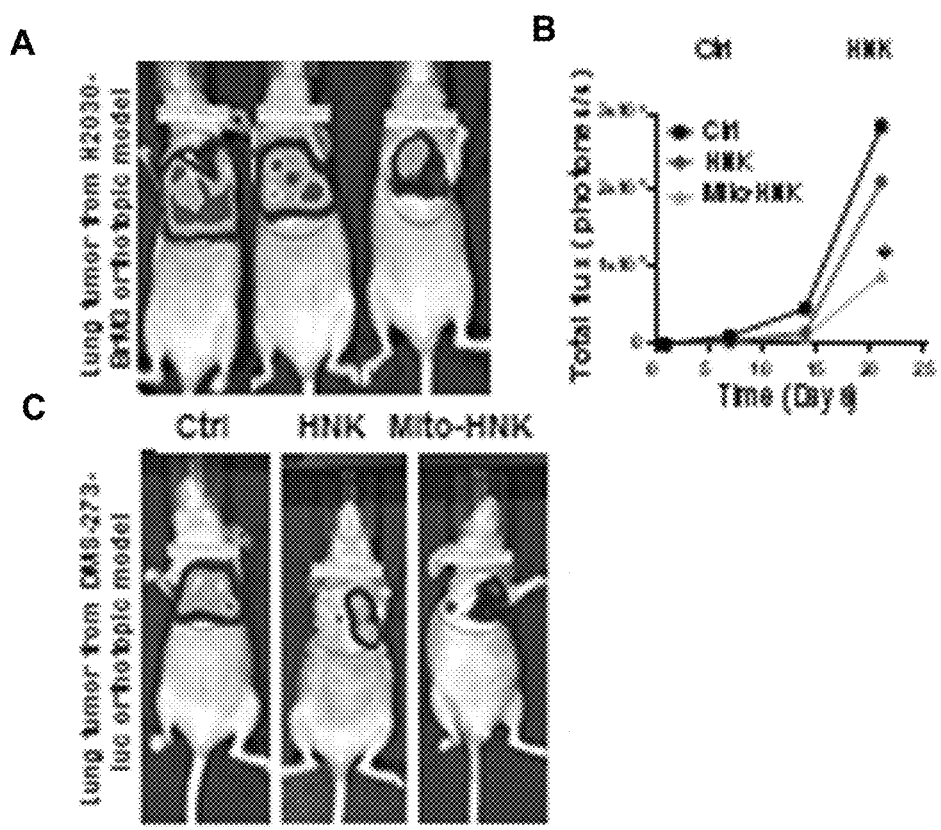
FIG. 11A-C. Mito-honokiol exhibits potent anti-cancer effects in NSLC or SCLC orthotopic lung cancer models. DM273 cells ($1\times10^6$ cells/50 μg of growth factor reduced Matrigel in 50 μL of RPMI-1640 medium) were injected into the left lung. One week after injection, mice were treated with the same dose of HNK or Mito-HNK (7.5 μmol/kg) or vehicle (corn oil) by oral gavage five times per week for three weeks). Representative images of bioluminescence are shown for H2030 injected mice (11A) and DMS273 injected mice (11C). While HNK did not significantly reduce tumor growth, Mito-HNK at the same dose reduced tumor size by 70% as compared to control mice (FIG. 11B).

In both the H2030-BrM3 and DMS-273 orthotopic lung cancer models, lung tumors grew within the left lung and then spread within the lung, to the mediastinum, and to the chest wall of the left hemithorax. Mice did not show any observable side effects when treated with HNK or Mito-HNK. Remarkably, Mito-HNK significantly reduced lymphatic tumor metastasis compared to that of the groups treated with either vehicle control or HNK (FIG. 11).

Mito-HNK Inhibits Both NSCLC and SCLC Brain Metastasis In Vivo

Figure 12:
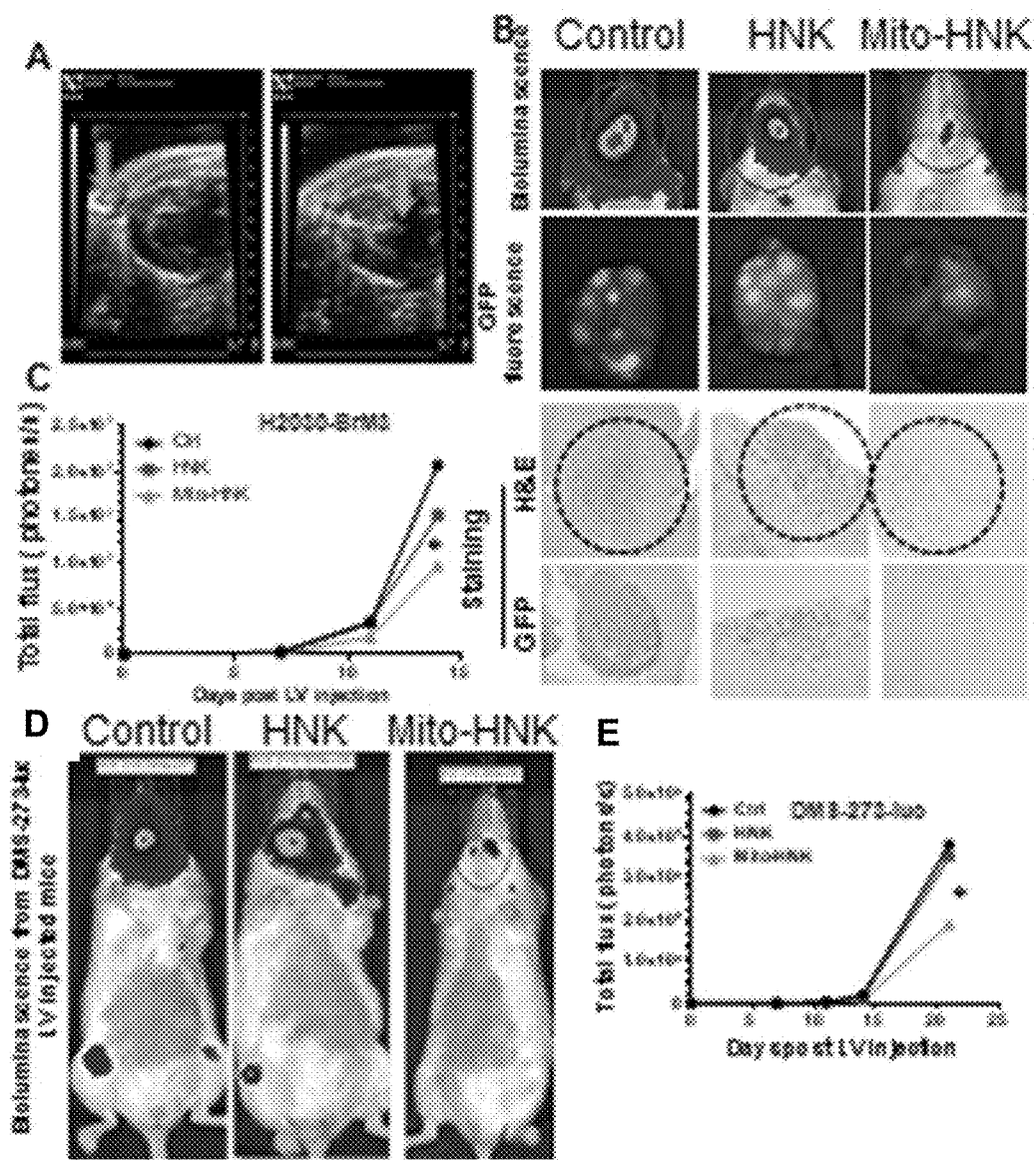
FIG. 12A-E. Mito-honokiol inhibits both NSCLC and SCLC brain metastasis in Nod/Scid mice. (A) Representative images of an ultrasound guided left ventricle injection for lung cancer brain metastasis models. (B) Representative luciferase, GFP, and H&E IHC images from the gavage control group and HNK- or Mito-HNK-treated group mice. (C) Quantification of bioluminescence imaging signal intensity in the control group and HNK-treated group at different time points after injection of H2030-BrM3 cells. Quantified values are shown in total flux. (D) Corresponding grayscale photographs and color luciferase images of DMS273-injected mice. Images are superimposed and analyzed with Living Image software (Xenogen Corporation). Data are expressed as normalized photon flux (photons/s/cm$^2$). (E) Graph depicting the quantification of bioluminescence imaging signal intensity for the control group and HNK- and Mito-HNK-treated groups at different time points after injection of DMS273 cells.
Figure 13:
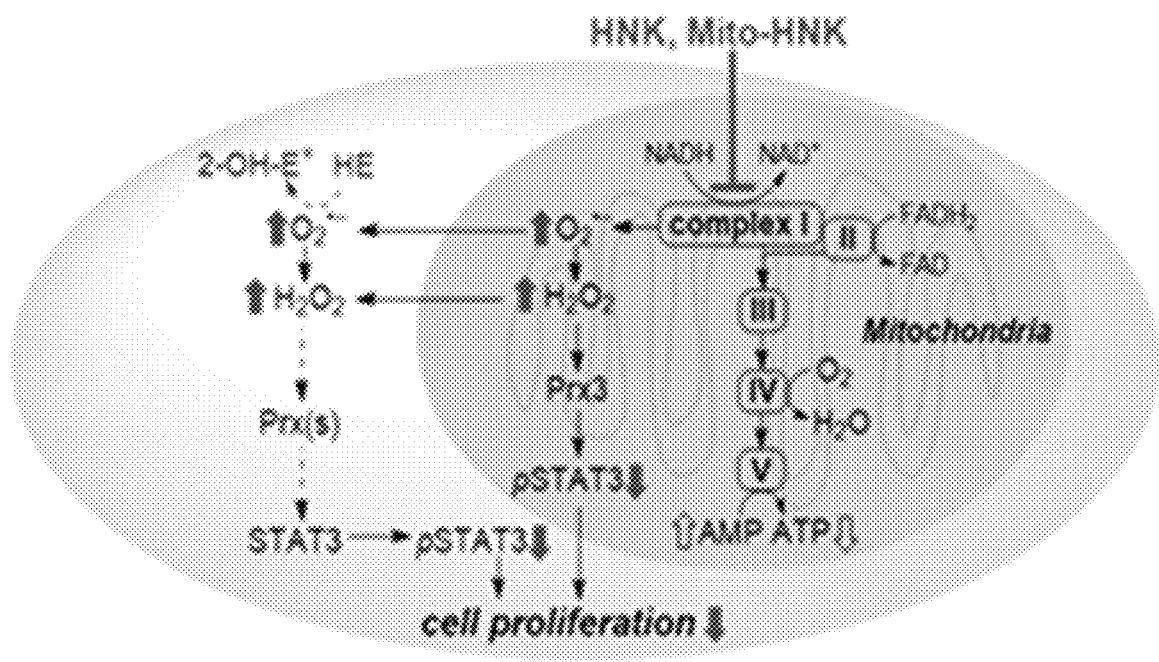
FIG. 13. Proposed mito-honokiol action mechanisms. Mito-HNK inhibits complex I, stimulates ROS, oxidizes peroxiredoxins, and blocks STAT3 phosphorylation, leading to inhibition of cell proliferation. Changes due to the treatment are shown by red block arrows. HE conversion to 2-0H-E$^+$ is used for specific detection of superoxide.

To investigate the effect of Mito-HNK on metastasis, a previously characterized experimental lung cancer brain metastasis model was used to generate brain metastases (Nguyen et al., 2009). We also generated GFP-luciferase expressing DMS-273 SCLC cells and confirmed brain metastasis of DMS-273 cells. We used an ultrasound-guided procedure to secure the precise injection of brain-seeking lung cancer cells into the left ventricle of NOD/SCID mice (FIG. 12A). One day after cell inoculation, the mice were randomly put into vehicle control, HNK, and Mito-HNK groups; tumor growth/brain metastases were monitored over 15 days using bioluminescence with an Xenogen IVIS-200. Mito-HNK-treated mice showed significantly fewer brain metastases compare to vehicle-control- or HNK-treated groups (FIG. 12C). At necropsy on 15 days post left-ventricle injection, brain metastases were qualified by ex vivo bioluminescence imaging, H&E and GFP staining as shown in FIG. 12B. Mito-HNK treatment decreased brain metastasis to nearly one-third of that of the control, as measured by luminescence intensity in the mouse brain. (FIGS. 12D,E). These data suggest that Mito-HNK could be a potent agent in preventing lung cancer brain metastases.

Discussion

Lung cancer is the leading cause of cancer mortality in the United States, and the metastatic spread of tumor cells to the brain is a major contributor to lung-cancer-related mortality (Goldberg et al., 2015; Jemal et al., 2010). A key approach to controlling this disease is the prevention of lung cancer development as well as its progression, especially metastases. Current available therapies to address CNS metastases include whole brain/CNS irradiation or surgical resection in eligible patients, and treatment with anti-EGFR agents in patients with EGFR mutations (Goldberg et al., 2015). However, these treatment options are available only after the diagnoses of brain tumors and at certain disease stages, whereas in many cases these metastasized tumors remain undiagnosed for a long time or are unable to be treated with either radiation therapy or surgery. Therefore, development of systematic prevention options to control metastases before diagnosis is necessary. Recently, we demonstrated the potent efficacy of HNK in the chemoprevention of lung tumor development in mice (Pan et al., 2014). Analysis of HNK's mechanism of action suggests that its effect is primarily mediated by inducing apoptosis through a mitochondria-dependent mechanism (Lin et al., 2012; Martin et al., 2013; Pan et al., 2014). Here, by using novel mitochondria-targeted HNK with a well-documented brain metastasis murine model, we report that Mito-HNK exerts an inhibition effect on lung cancer brain metastases, and we demonstrate HNK as a potential chemoprevention agent not only effective in primary lung tumor but also on lung cancer brain metastases.

Direct injection of tumor cells into the left ventricle is the most widely used brain metastasis model in rodents; though it bypasses precolonization steps such as dissemination, extravasation, and homing, it recapitulates the cancer cells' BBB crossing, invasion, and outgrowth in the brain microenvironment. Metastatic brain lesions vary from round, circumscribed lesions typical of those seen in humans, to very infiltrative tumor cells, which, if given time, will form typical round lesions; such lesions are ideal for use in evaluating the preventive effect of Mito-HNK on lung cancer metastasis. The brain homing H2030 and PC9 cell lines were developed to have 100% brain-metastatic potential, H2030 with a KRASG12C mutation (Phelps et al., 1996), and PC9 with an EGFRΔexon19 mutation (Koizumi et al., 2005). These cells were engineered to stably express GFP-luciferase fusion for real-time monitoring of metastatic tumor growth. In our study, we monitored metastatic tumor growth by both live animal imaging and endpoint ex vivo imaging. Also, tumor growth was validated with H&E and GFP staining assays, which consistently showed nearly 70% inhibition on brain metastases.

In this study, we represent that Mito-HNK effectively inhibits brain metastatic lung cancer proliferation, migration, and invasion mainly through inhibition of mitochondria complex I-STAT3 phosphorylation. HNK has been reported to target multiple signaling pathways including EGFR, MAPK, and PI3K-Akt (Crane et al., 2009; Deng et al., 2008; Garcia et al., 2008; Tse et al., 2005). Recently, SIRT3 and GRP78 also were suggested as potential binding targets of HNK in different tissue types (Martin et al., 2013; Pillai et al., 2015). Interestingly, STAT3 is a major downstream mediator of multiple receptor tyrosine kinase pathways (De Simone et al., 2015; Wu et al., 2014; Yau et al., 2005; Zhou et al., 2007).

In this study we also demonstrate that, regardless of EGFR mutation status, Mito-HNK decreased STAT3 phosphorylation in both PC9-BrM3 and H2030-BrM3 brain metastatic lung cancer cell lines. In addition, the knock down of endogenous STAT3 abrogated the antiproliferative, antimigratory, and anti-invasive effects of Mito-HNK in both brain metastatic lung cancer cell lines. Our data suggest that STAT3 could be a universal downstream target of Mito-HNK, regardless of the lung cancer's driver mutation status.

The development of new and effective therapies for patients with either brain metastatic NSCLC or highly metastatic SCLC is urgently needed. Targeting cancer metabolism is a novel therapeutic strategy to treat lung cancers. Here, we demonstrate a new mitochondria-targeted compound, Mito-HNK, to facilitate its delivery of HNK to mitochondria. We successfully demonstrate the therapeutic potential of Mito-HNK using both in vitro and in vivo models and determine its mechanism of action. The Mito-HNK provides novel preventive and therapeutic options for lung cancer patients with brain metastases.

Example 9. Additional In Vitro Testing

Figure 14A:
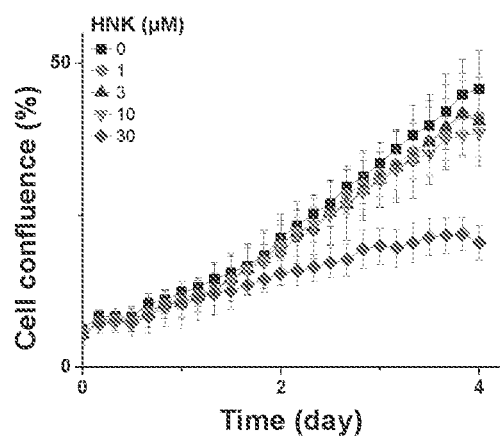
FIG. 14A-D. Effects of mito-honokiol in a brain cancer cell line. The effects of Mito-HNK (14B and 14C) and Bis-Mito-HNK (14D) on U87 cells, a brain cancer cell line, is shown as compared with HNK alone (FIG. 14A).
Figure 14B:
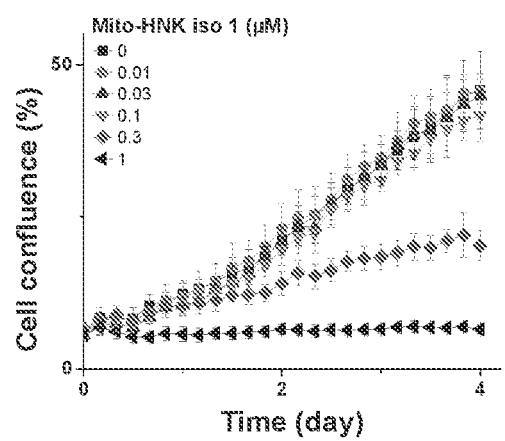
Figure 14C:
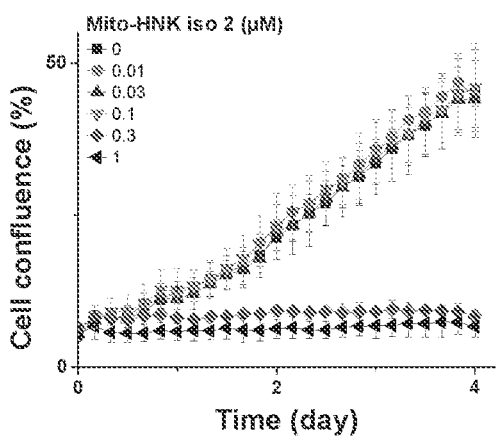
Figure 14D:
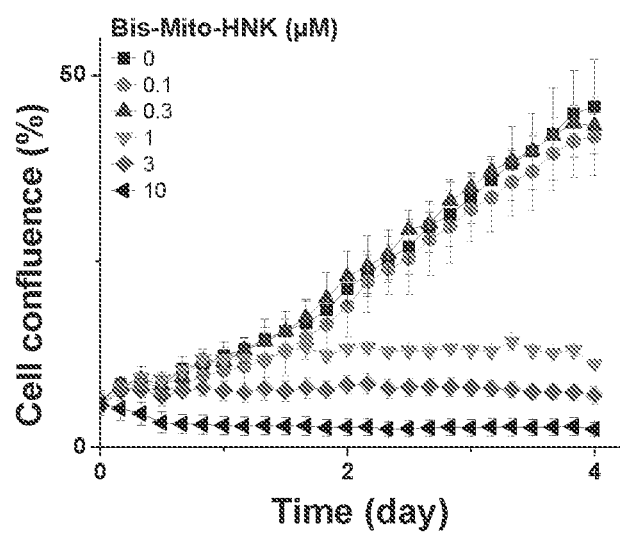

Using similar methods as described in Example 8, Mito-HNK was tested in other tumor cell lines. FIG. 14B-D shows the effects of Mito-HNK (14B and 14C) and Bis-Mito-HNK (14D) on U87 cells, a brain cancer cell line, as compared with HNK alone (FIG. 14A). Thus, Mito-HNK can be used to reduce and inhibit brain cancer.

Figure 15A:
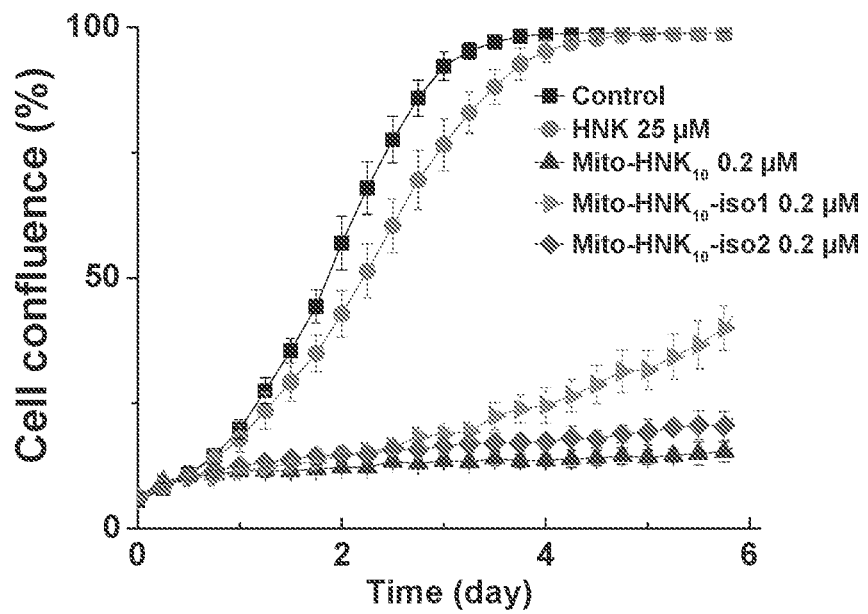
FIG. 15-A-F. Effects of mito-honokiol alone or in combination with 2-deoxyglucose on pancreatic cells. At sub-micromolar concentration (0.2 µM) both isomers of Mito-HNK—$C_{10}$ inhibit proliferation of MiaPaCa-2 cells (pancreatic cancer cell line) (FIG. 15A). Mito-magnolol (1 µM) and isomers of mito-honokiol-$C_4$ also exhibit antiproliferative effects (FIG. 15B). Further, the combining the mito-honokiols of the present invention with antiglycolytic agents (e.g. 2-deoxyglucose) reduced the rate of proliferation of pancreatic cancer cells than either treatment alone, as shown for a number of different concentrations in FIG. 15C-F.
Figure 15B:
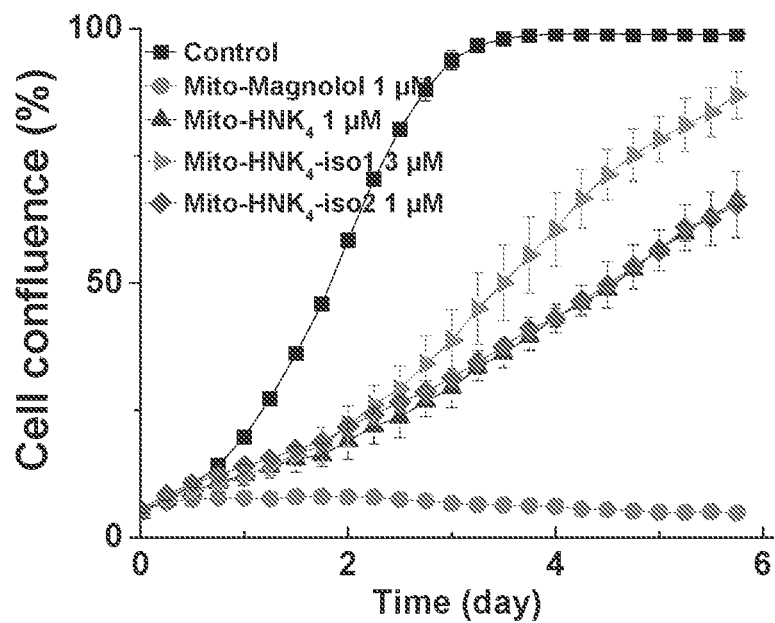
Figure 15C:
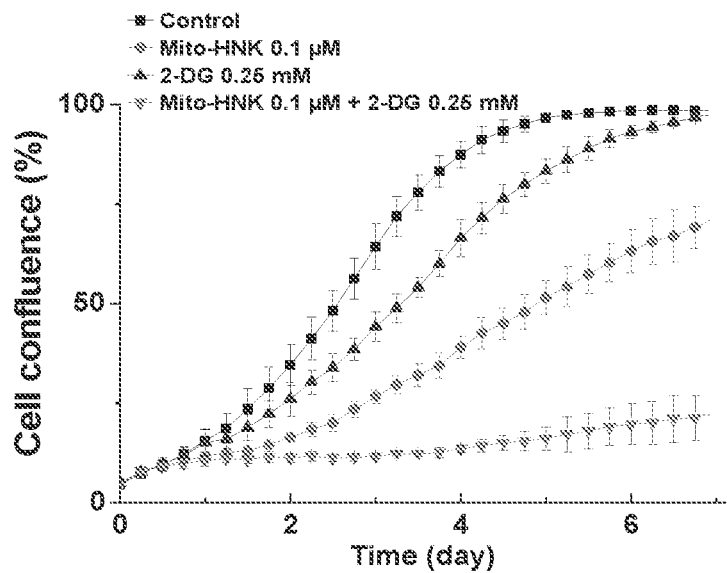
Figure 15D:
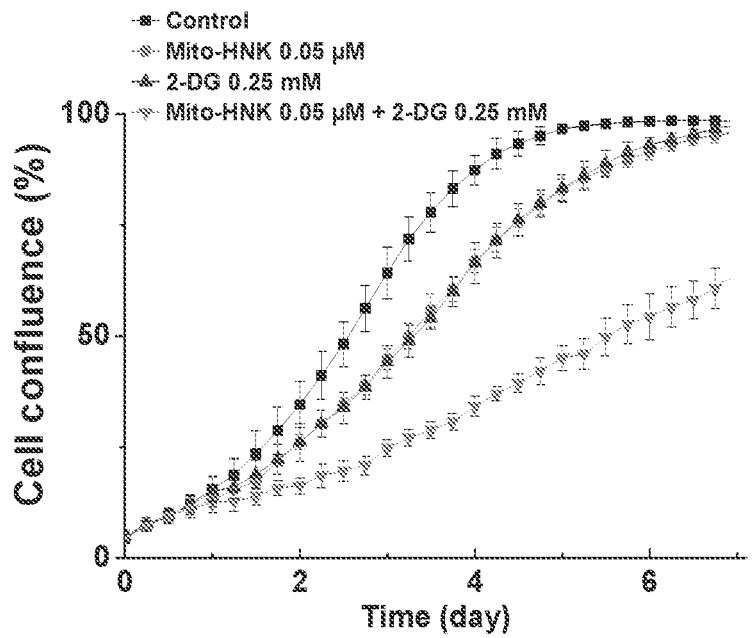
Figure 15E:
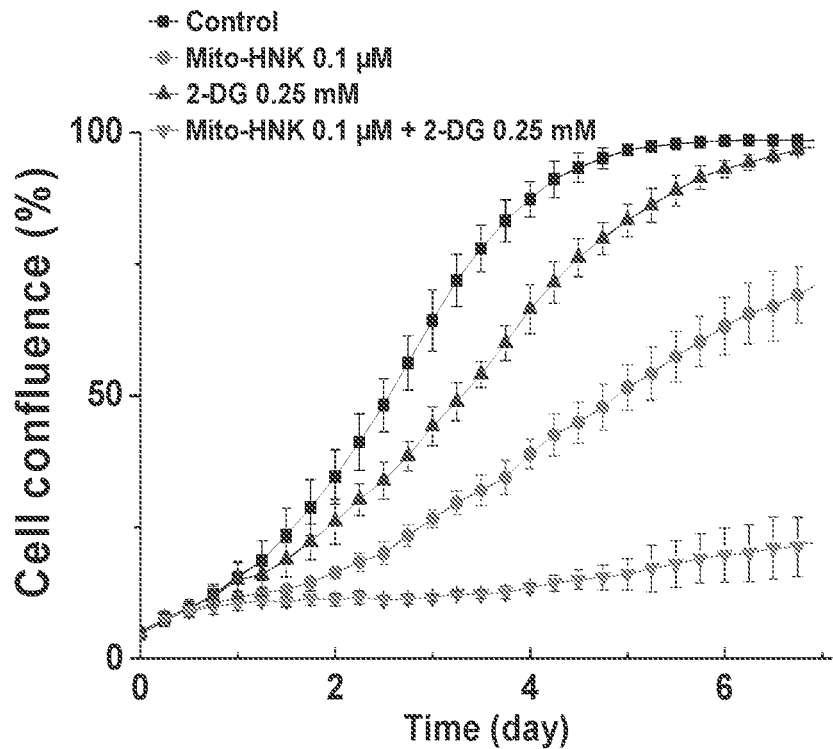
Figure 15F:
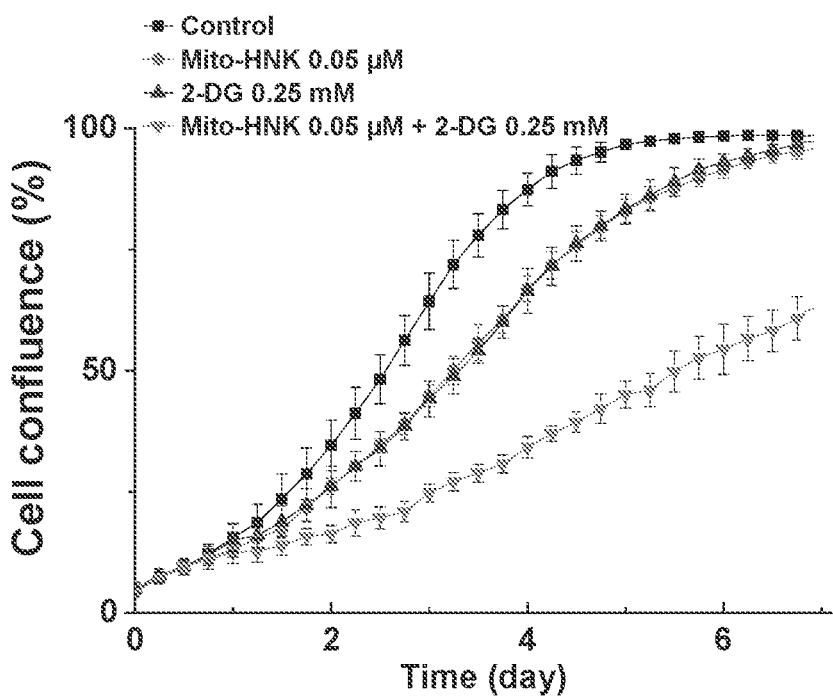
Figure 16A:
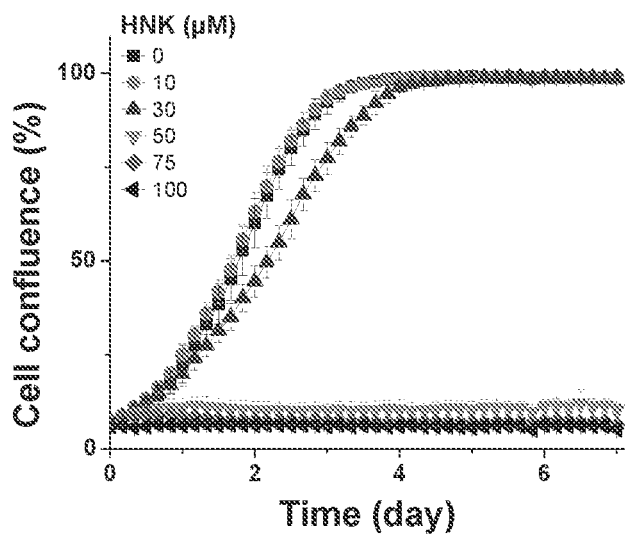
FIG. 16A-B. In vitro effects of mito-magnolol. In vitro inhibition of cell growth for MiaPaCa cells for HNK alone (FIG. 16A), magnolol (FIG. 16B), as compared to mito-magnolol (FIG. 16C) and mito-phenyl-HNK (FIG. 16D).
Figure 16B:
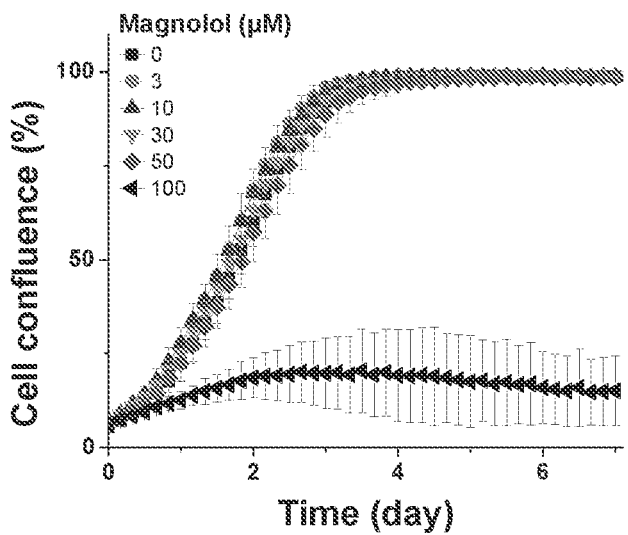
Figure 16C:
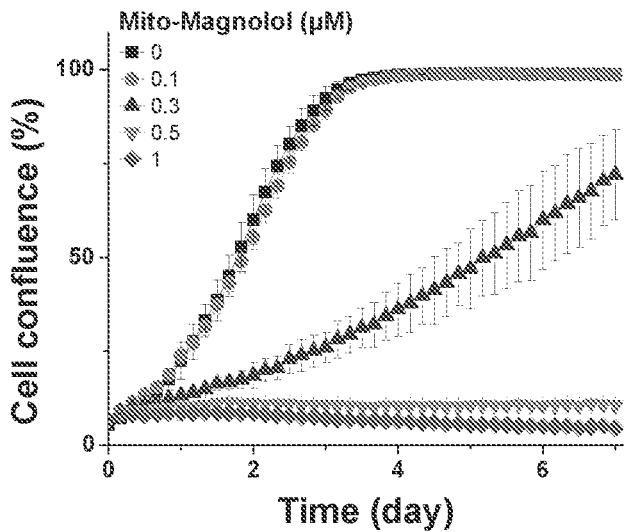
Figure 16D:
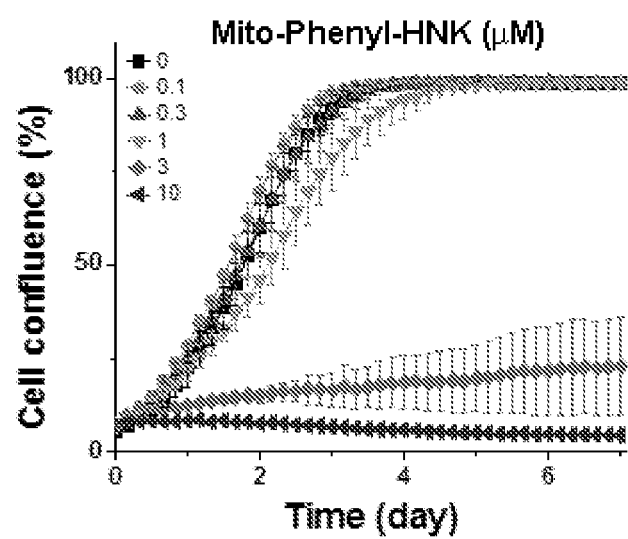

FIGS. 15A and B demonstrates the effect of Mito-HNK as compared with HNK at two different concentrations, 0.2 μM (FIG. 15A) and 1 μM (FIG. 15B) in MiaPaCa-2 cells (pancreatic cancer cell line). Further, the combining the mito-honokiols of the present invention with antiglycolytic agents (e.g. 2-deoxyglucose) reduced the rate of proliferation of pancreatic cancer cells than either treatment alone, as shown for a number of different concentrations in FIG. 15C-F. FIG. 16 further demonstrates in vitro inhibition of cell growth for MiaPaCa cells for HNK alone (FIG. 16A), magnolol (FIG. 16B), as compared to mito-magnolol (FIG. 16C) and mito-phenyl-HNK (FIG. 16D).

FIGS. 17A and B show the effects of the combination of mito-honokiols with 2-deoxyglucose on total ATP levels in Capan-2 cells (pancreatic adenocarcinoma cell line).

A REFERENCES

Alas, S., and Bonavida, B. (2003). Inhibition of constitutive STAT3 activity sensitizes resistant non-Hodgkin's lymphoma and multiple myeloma to chemotherapeutic drug-mediated apoptosis. Clin Cancer Res 9, 316-326.

Anders, S., Pyl, P. T., and Huber, W. (2015). HTSeq—a Python framework to work with high-throughput sequencing data. Bioinformatics 31, 166-169.

Bewry, N. N., Nair, R. R., Emmons, M. F., Boulware, D., Pinilla-Ibarz, J., and Hazlehurst, L. A. (2008). Stat3 contributes to resistance toward BCR-ABL inhibitors in a bone marrow microenvironment model of drug resistance. Mol Cancer Ther 7, 3169-3175.

Bradford, J. R., Farren, M., Powell, S. J., Runswick, S., Weston, S. L., Brown, H., Delpuech, O., Wappett, M., Smith, N. R., Carr, T. H., et al. (2013). RNA-Seq Differentiates Tumour and Host mRNA Expression Changes Induced by Treatment of Human Tumour Xenografts with the VEGFR Tyrosine Kinase Inhibitor Cediranib. PLoS One 8, e66003.

Chen, F., Wang, T., Wu, Y. F., Gu, Y., Xu, X. L., Zheng, S., and Hu, X. (2004). Honokiol: a potent chemotherapy candidate for human colorectal carcinoma. World J Gastroenterol 10, 3459-3463.

Chen, Y. J., Wu, C. L., Liu, J. F., Fong, Y. C., Hsu, S. F., Li, T. M., Su, Y. C., Liu, S. H., and Tang, C. H. (2010). Honokiol induces cell apoptosis in human chondrosarcoma cells through mitochondrial dysfunction and endoplasmic reticulum stress. Cancer Lett 291, 20-30.

Cheng, G., Zielonka, J., Dranka, B. P., McAllister, D., Mackinnon, A. C., Joseph, J., and Kalyanaraman, B. (2012). Mitochondria-targeted drugs synergize with 2-deoxyglucose to trigger breast cancer cell death. Cancer Res 72, 2634-2644.

Cheng, G., Zielonka, J., McAllister, D., Tsai, S., Dwinell, M. B., and Kalyanaraman, B. (2014). Profiling and targeting of cellular bioenergetics: inhibition of pancreatic cancer cell proliferation. Br J Cancer, 1-9.

Cheng, G., Zielonka, J., McAllister, D. M., Mackinnon, a. C., Joseph, J., Dwinell, M. B., and Kalyanaraman, B. (2013). Mitochondria-targeted vitamin E analogs inhibit breast cancer cell energy metabolism and promote cell death. BMC Cancer 13, 285-285.

Crane, C., Panner, A., Pieper, R. O., Arbiser, J., and Parsa, A. T. (2009). Honokiol-mediated inhibition of PI3K/mTOR pathway: a potential strategy to overcome immunoresistance in glioma, breast, and prostate carcinoma without impacting T cell function. J Immunother 32, 585-592.

De Simone, V., Franze, E., Ronchetti, G., Colantoni, A., Fantini, M. C., Di Fusco, D., Sica, G. S., Sileri, P., MacDonald, T. T., Pallone, F., et al. (2015). Th17-type cytokines, IL-6 and TNF-alpha synergistically activate STAT3 and NF-kB to promote colorectal cancer cell growth. Oncogene 34, 3493-3503.

Deng, J., Qian, Y., Geng, L., Chen, J., Wang, X., Xie, H., Yan, S., Jiang, G., Zhou, L., and Zheng, S. (2008). Involvement of p38 mitogen-activated protein kinase pathway in honokiol-induced apoptosis in a human hepatoma cell line (hepG2). Liver Int 28, 1458-1464.

Gane, E. J., Weilert, F., Orr, D. W., Keogh, G. F., Gibson, M., Lockhart, M. M., Frampton, C. M., Taylor, K. M., Smith, R. A., and Murphy, M. P. (2010). The mitochondria-targeted anti-oxidant mitoquinone decreases liver damage in a phase II study of hepatitis C patients. Liver Int 30, 1019-1026.

Garcia, A., Zheng, Y., Zhao, C., Toschi, A., Fan, J., Shraibman, N., Brown, H. A., Bar-Sagi, D., Foster, D. A., and Arbiser, J. L. (2008). Honokiol suppresses survival signals mediated by Ras-dependent phospholipase D activity in human cancer cells. Clin Cancer Res 14, 4267-4274.

Goldberg, S. B., Contessa, J. N., Omay, S. B., and Chiang, V. (2015). Lung Cancer Brain Metastases. Cancer J 21, 398-403.

Hahm, E. R., and Singh, S. V. (2007). Honokiol causes G0-G1 phase cell cycle arrest in human prostate cancer cells in association with suppression of retinoblastoma protein level/phosphorylation and inhibition of E2F1 transcriptional activity. Mol Cancer Ther 6, 2686-2695.

Jemal, A., Siegel, R., Xu, J., and Ward, E. (2010). Cancer statistics, 2010. CA: a cancer journal for clinicians 60, 277-300.

Koizumi, F., Shimoyama, T., Taguchi, F., Saijo, N., and Nishio, K. (2005). Establishment of a human non-small cell lung cancer cell line resistant to gefitinib. Int J Cancer 116, 36-44.

Langmead, B., Trapnell, C., Pop, M., and Salzberg, S. L. (2009). Ultrafast and memory-efficient alignment of short DNA sequences to the human genome. Genome Biol 10, R25.

Lee, H. J., Zhuang, G., Cao, Y., Du, P., Kim, H. J., and Settleman, J. (2014). Drug resistance via feedback activation of Stat3 in oncogene-addicted cancer cells. Cancer Cell 26, 207-221.

Lee, Y., Wang, Y., James, M., Jeong, J. H., and You, M. (2016). Inhibition of IGF1R signaling abrogates resistance to afatinib (BIBW2992) in EGFR T790M mutant lung cancer cells. Mol Carcinog 55, 991-1001.

Li, P., Zhang, D., Shen, L., Dong, K., Wu, M., Ou, Z., and Shi, D. (2016). Redox homeostasis protects mitochondria through accelerating ROS conversion to enhance hypoxia resistance in cancer cells. Sci Rep 6, 22831.

Lin, J. W., Chen, J. T., Hong, C. Y., Lin, Y. L., Wang, K. T., Yao, C. J., Lai, G. M., and Chen, R. M. (2012). Honokiol traverses the blood-brain barrier and induces apoptosis of neuroblastoma cells via an intrinsic bax-mitochondrion-cytochrome c-caspase protease pathway. Neuro Oncol 14, 302-314.

Lin, L., Liu, A., Peng, Z., Lin, H. J., Li, P. K., Li, C., and Lin, J. (2011). STAT3 is necessary for proliferation and survival in colon cancer-initiating cells. Cancer Res 71, 7226-7237.

Martin, S., Lamb, H. K., Brady, C., Lefkove, B., Bonner, M. Y., Thompson, P., Lovat, P. E., Arbiser, J. L., Hawkins, A. R., and Redfern, C. P. (2013). Inducing apoptosis of cancer cells using small-molecule plant compounds that bind to GRP78. Br J Cancer 109, 433-443.

McManus, M. J., Murphy, M. P., and Franklin, J. L. (2011). The mitochondria-targeted antioxidant MitoQ prevents loss of spatial memory retention and early neuropathology in a transgenic mouse model of Alzheimer's disease. J Neurosci 31, 15703-15715.

Nair, R. R., Tolentino, J. H., and Hazlehurst, L. A. (2012). Role of STAT3 in Transformation and Drug Resistance in CML. Front Oncol 2, 30.

Nguyen, D. X., Chiang, A. C., Zhang, X. H., Kim, J. Y., Kris, M. G., Ladanyi, M., Gerald, W. L., and Massague, J. (2009). WNT/TCF signaling through LEF1 and HOXB9 mediates lung adenocarcinoma metastasis. Cell 138, 51-62.

Pan, J., Zhang, Q., Liu, Q., Komas, S. M., Kalyanaraman, B., Lubet, R. A., Wang, Y., and You, M. (2014). Honokiol inhibits lung tumorigenesis through inhibition of mitochondrial function. Cancer Prev Res (Phila) 7, 1149-1159.

Park, E. J., Min, H. Y., Chung, H. J., Hong, J. Y., Kang, Y. J., Hung, T. M., Youn, U. J., Kim, Y. S., Bae, K., Kang, S. S., and Lee, S. K. (2009). Down-regulation of c-Src/EGFR-mediated signaling activation is involved in the honokiol-induced cell cycle arrest and apoptosis in MDA-MB-231 human breast cancer cells. Cancer Lett 277, 133-140.

Phelps, R. M., Johnson, B. E., Ihde, D. C., Gazdar, A. F., Carbone, D. P., McClintock, P. R., Linnoila, R. I., Matthews, M. J., Bunn, P. A., Jr., Carney, D., et al. (1996). NCI-Navy Medical Oncology Branch cell line data base. J Cell Biochem Suppl 24, 32-91.

Pillai, V. B., Samant, S., Sundaresan, N. R., Raghuraman, H., Kim, G., Bonner, M. Y., Arbiser, J. L., Walker, D. I., Jones, D. P., Gius, D., and Gupta, M. P. (2015). Honokiol blocks and reverses cardiac hypertrophy in mice by activating mitochondrial Sirt3. Nat Commun 6, 6656.

Robinson, M. D., McCarthy, D. J., and Smyth, G. K. (2010). edgeR: a Bioconductor package for differential expression analysis of digital gene expression data. Bioinformatics 26, 139-140.

Rossello, F. J., Tothill, R. W., Britt, K., Marini, K. D., Falzon, J., Thomas, D. M., Peacock, C. D., Marchionni, L., Li, J., Bennett, S., et al. (2013). Next-generation sequence analysis of cancer xenograft models. PLoS One 8, e74432.

Trapnell, C., Pachter, L., and Salzberg, S. L. (2009). TopHat: discovering splice junctions with RNA-Seq. Bioinformatics 25, 1105-1111.

Tsai, T. H., Chou, C. J., Cheng, F. C., and Chen, C. F. (1994). Pharmacokinetics of honokiol after intravenous administration in rats assessed using high-performance liquid chromatography. J Chromatogr B Biomed Appl 655, 41-45.

Tse, A. K., Wan, C. K., Shen, X. L., Yang, M., and Fong, W. F. (2005). Honokiol inhibits TNF-alpha-stimulated NF-kappaB activation and NF-kappaB-regulated gene expression through suppression of IKK activation. Biochem Pharmacol 70, 1443-1457.

Vazquez-Martin, A., Cufi, S., Oliveras-Ferraros, C., Torres-Garcia, V. Z., Corominas-Faja, B., Cuyas, E., Bonavia, R., Visa, J., Martin-Castillo, B., Barrajon-Catalan, E., et al. (2013). IGF-1R/epithelial-to-mesenchymal transition (EMT) crosstalk suppresses the erlotinib-sensitizing effect of EGFR exon 19 deletion mutations. Sci Rep 3, 2560.

Wang, X., Duan, X., Yang, G., Zhang, X., Deng, L., Zheng, H., Deng, C., Wen, J., Wang, N., Peng, C., et al. (2011). Honokiol crosses BBB and BCSFB, and inhibits brain tumor growth in rat 9L intracerebral gliosarcoma model and human U251 xenograft glioma model. PLoS One 6, e18490.

Wu, J., Patmore, D. M., Jousma, E., Eaves, D. W., Breving, K., Patel, A. V., Schwartz, E. B., Fuchs, J. R., Cripe, T. P., Stemmer-Rachamimov, A. O., and Ratner, N. (2014). EGFR-STAT3 signaling promotes formation of malignant peripheral nerve sheath tumors. Oncogene 33, 173-180.

Yang, H., Yamazaki, T., Pietrocola, F., Zhou, H., Zitvogel, L., Ma, Y., and Kroemer, G. (2015). STAT3 Inhibition Enhances the Therapeutic Efficacy of Immunogenic Chemotherapy by Stimulating Type 1 Interferon Production by Cancer Cells. Cancer Res 75, 3812-3822.

Yau, C. Y., Wheeler, J. J., Sutton, K. L., and Hedley, D. W. (2005). Inhibition of integrin-linked kinase by a selective small molecule inhibitor, QLT0254, inhibits the PI3K/PKB/mTOR, Stat3, and FKHR pathways and tumor growth, and enhances gemcitabine-induced apoptosis in human orthotopic primary pancreatic cancer xenografts. Cancer Res 65, 1497-1504.

Yu, P., Yu, H., Guo, C., Cui, Z., Chen, X., Yin, Q., Zhang, P., Yang, X., Cui, H., and Li, Y. (2015). Reversal of doxorubicin resistance in breast cancer by mitochondria-targeted pH-responsive micelles. Acta Biomater 14, 115-124.

Zhang, Q., Raje, V., Yakovlev, V. A., Yacoub, A., Szczepanek, K., Meier, J., Derecka, M., Chen, Q., Hu, Y., Sisler, J., et al. (2013). Mitochondrial localized Stat3 promotes breast cancer growth via phosphorylation of serine 727. J Biol Chem 288, 31280-31288.

Zhou, J., Wulfkuhle, J., Zhang, H., Gu, P., Yang, Y., Deng, J., Margolick, J. B., Liotta, L. A., Petricoin, E., 3rd, and Zhang, Y. (2007). Activation of the PTEN/mTOR/STAT3 pathway in breast cancer stem-like cells is required for viability and maintenance. Proc Natl Acad Sci USA 104, 16158-16163.

We claim:

1. A modified honokiol compound according to the following structure:

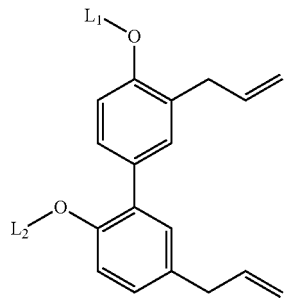

Where $L_1$ and $L_2$ are selected from the group consisting of:

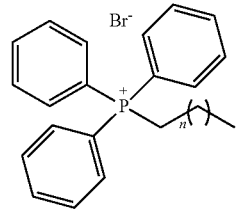

n = 1-12 and H, where $L_1$ and $L_2$ cannot be H at the same time.

2. The mito-honokiol compound of claim 1, wherein the mito-honokiol compound is according to the following structure:

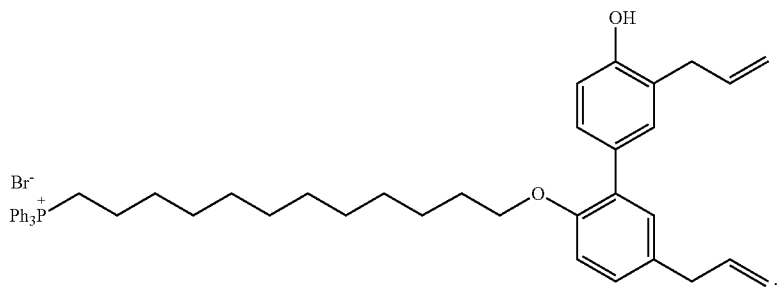

($2'$-Mito$_{12}$-Honokiol)

3. The mito-honokiol compound of claim 1, wherein the mito-honokiol is according to the following structure:

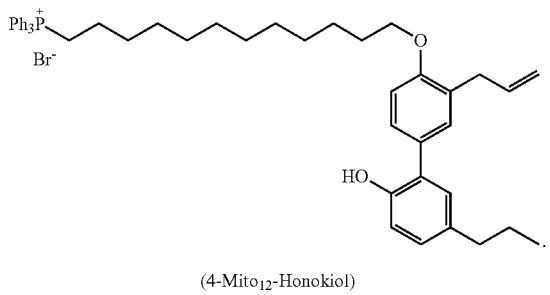

(4-Mito₁₂-Honokiol)

4. The mito-honokiol compound of claim 1, wherein the mito-honokiol is according to the following structure:

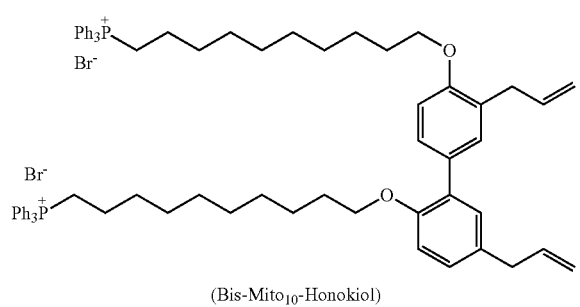

(Bis-Mito₁₀-Honokiol)

5. The mito-honokiol compound of claim 1, wherein the mito-honokiol is according to the following structure:

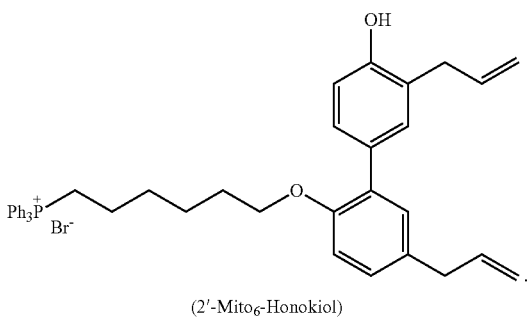

(2'-Mito₆-Honokiol)

6. The mito-honokiol compound of claim 1, wherein the mito-honokiol is according to the following structure:

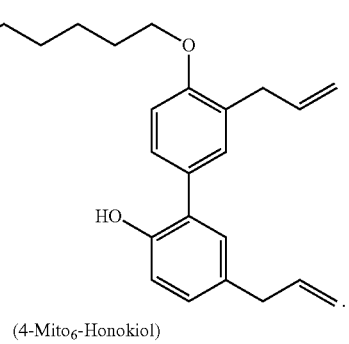

(4-Mito₆-Honokiol)

7. The mito-honokiol compound of claim 1, wherein the mito-honokiol is according to the following structure:

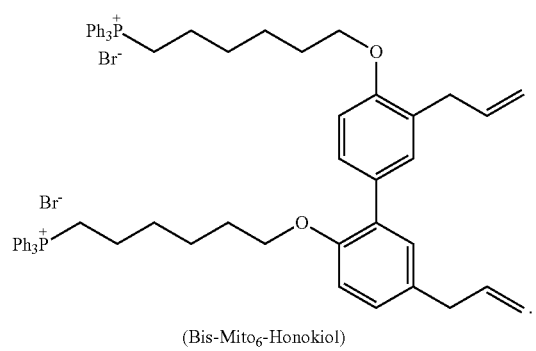

(Bis-Mito₆-Honokiol)

8. The mito-honokiol compound of claim 1, wherein the mito-honokiol is according to the following structure:

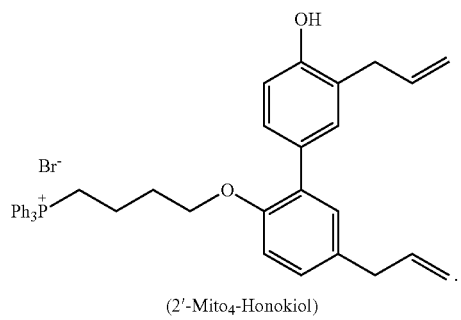

(2'-Mito₄-Honokiol)

9. The mito-honokiol compound of claim 1, wherein the mito-honokiol is according to the following structure:

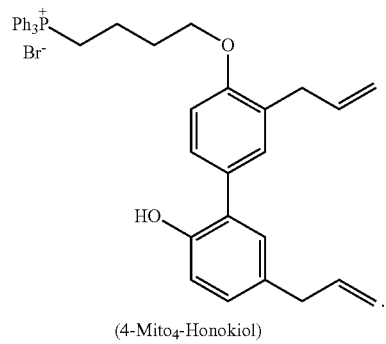

(4-Mito₄-Honokiol)

10. The mito-honokiol compound of claim 1, wherein the mito-honokiol is according to the following structure:

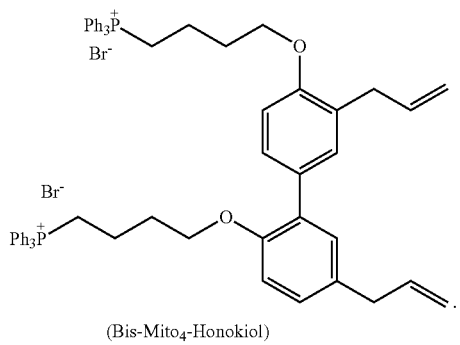

(Bis-Mito₄-Honokiol)

11. The mito-honokiol compound of claim 1, wherein the mito-honokiol is according to the following structure:

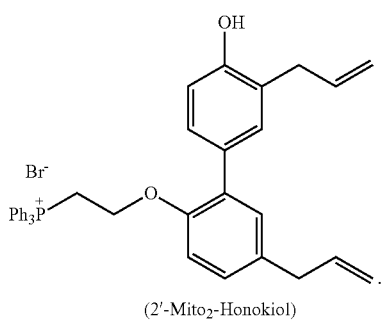

(2'-Mito₂-Honokiol)

12. The mito-honokiol compound of claim 1, wherein the mito-honokiol is according to the following structure:

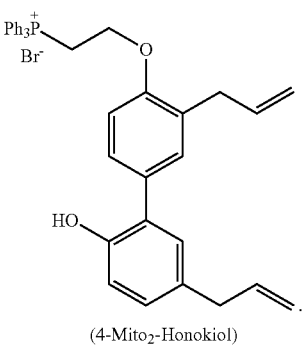

(4-Mito₂-Honokiol)

13. The mito-honokiol compound of claim 1, wherein the mito-honokiol is according to the following structure:

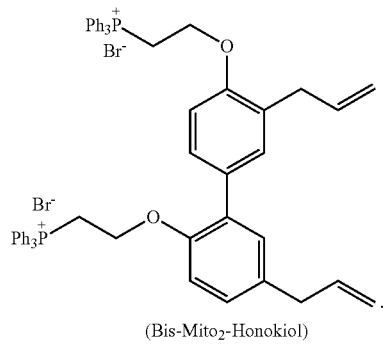

(Bis-Mito₂-Honokiol)

14. A mito-honokiol is according to the following structure:

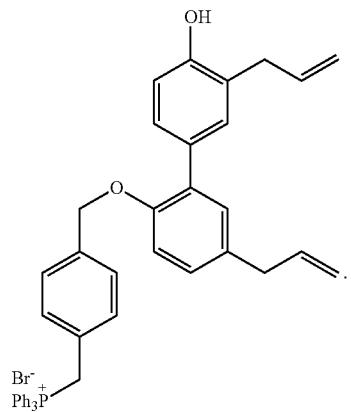

(2'-Mito_phen-Honokiol)

15. A mito-honokiol is according to the following structure:

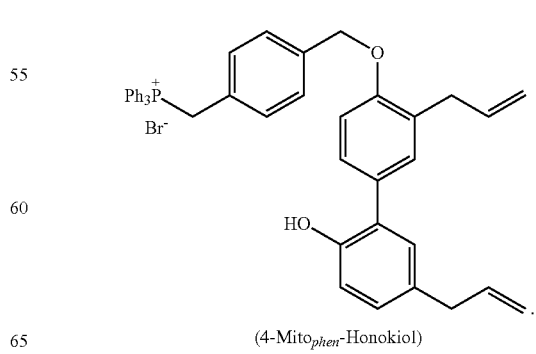

(4-Mito_phen-Honokiol)

16. A mito-honokiol is according to the following structure:

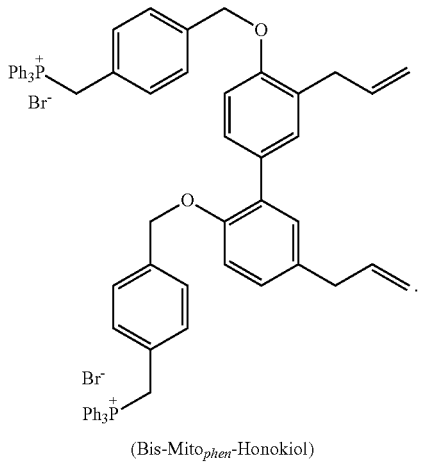

(Bis-Mito$_{phen}$-Honokiol)

17. A method of reducing or inhibiting tumor growth in a subject comprising administering to the subject a therapeutically effective amount of a composition comprising at least one mito-honokiol compound of claim 1, wherein the tumor is lung cancer or pancreatic cancer.

18. A kit comprising at least one mito-honokiol compound of claim 1, a pharmaceutically acceptable carrier or diluent, and instructional material.

19. The method of claim 17, wherein the tumor is a lung cancer.

20. The method of claim 17, wherein the tumor is a metastatic tumor.

21. The method of claim 17, wherein the cancer in the patient is a primary cancer or a secondary metastatic tumor thereof.

22. The method of claim 17, wherein the method further comprises treatment of the patient with an antiglycolytic agent and other standard-of-care drug.

23. The method of claim 22, wherein the antiglycolytic agent is selected from the group consisting of 2-deoxyglucose or 3-bromopyruvate.

24. The method of claim 17, wherein the method further comprises treating the patient with surgery, radiation therapy (RT), or chemotherapy (CT) prior to or concurrently with administering the pharmaceutical composition.

25. A method of inhibiting, or reducing metastasis of a cancer comprising administering an effective amount of a pharmaceutical composition comprising at least one mito-honokiol of claim 1 to inhibit or reduce metastasis of cancer in the patient, wherein the cancer is selected from the group consisting of lung cancer and pancreatic cancer.

26. The method of claim 25, wherein the metastasis is in a lymph node or distal organ.

27. The method of claim 26, wherein the metastasis is in the brain.

* * * * *